(12) United States Patent
Iannotti et al.

(10) Patent No.: US 9,439,768 B2
(45) Date of Patent: Sep. 13, 2016

(54) GLENOID VAULT FIXATION

(75) Inventors: Joseph P. Iannotti, Strongsville, OH (US); Gerald Williams, Villanova, PA (US); Dinesh Koka, Orlando, FL (US); Michael Chad Hollis, Winter Springs, FL (US)

(73) Assignees: IMDS LLC, Providence, UT (US); Cleveland Clinic Foundation, Cleveland, OH (US)

( * ) Notice: Subject to any disclaimer, the term of this patent is extended or adjusted under 35 U.S.C. 154(b) by 662 days.

(21) Appl. No.: 13/360,459

(22) Filed: Jan. 27, 2012

(65) Prior Publication Data
US 2013/0150972 A1 Jun. 13, 2013

Related U.S. Application Data

(60) Provisional application No. 61/568,530, filed on Dec. 8, 2011.

(51) Int. Cl.
| | | |
|---|---|---|
| A61F 2/30 | (2006.01) | |
| A61F 2/40 | (2006.01) | |
| A61F 2/46 | (2006.01) | |
| A61F 2/28 | (2006.01) | |
| A61B 17/86 | (2006.01) | |

(52) U.S. Cl.
CPC ......... *A61F 2/4081* (2013.01); *A61F 2/30734* (2013.01); *A61F 2/30749* (2013.01); *A61F 2/4003* (2013.01); *A61F 2/4059* (2013.01); *A61F 2/4637* (2013.01); *A61B 17/86* (2013.01); *A61F 2/4014* (2013.01); *A61F 2002/2835* (2013.01); *A61F 2002/305* (2013.01); *A61F 2002/3054* (2013.01); *A61F 2002/3085* (2013.01); *A61F 2002/30331* (2013.01);

(Continued)

(58) Field of Classification Search
CPC .......... A61F 2/4081; A61F 2/40; A61F 2/30
USPC ....................................... 623/19.11
See application file for complete search history.

(56) References Cited

U.S. PATENT DOCUMENTS

| 1,105,105 A | 7/1914 | Sherman |
|---|---|---|
| 2,580,821 A | 1/1952 | Nicola |

(Continued)

FOREIGN PATENT DOCUMENTS

| DE | 3630276 | 3/1988 |
|---|---|---|
| DE | 10 2006 041551 A1 | 11/2007 |

(Continued)

OTHER PUBLICATIONS

Fucentese, Sandro; Total shoulder Arthroplasty with an Uncemented Soft-Metal-Backed Glenoid Component, Journal of shoulder elbow Surgery (2010) 19, 624-631.

(Continued)

*Primary Examiner* — Matthew Schall
(74) *Attorney, Agent, or Firm* — Brinks Gilson & Lione; Craig Buschmann

(57) ABSTRACT

A joint prosthesis system, specifically a shoulder prosthesis, for shoulder replacement, revision and repair. The implants provide fixation into the best bone available to a surgeon. The implants are used in a superior-inferior and anterior-posterior construct forming a type of cross or X-shape. The implants allow for interchangeability of the articulating component as well as rotational orientation. The systems will allow for augments to accommodate bone loss. The implants may allow for additional security using screws or anchors inserted into the scapula.

45 Claims, 40 Drawing Sheets

(52) U.S. Cl.
CPC .......... A61F2002/30332 (2013.01); A61F 2002/30367 (2013.01); A61F 2002/30387 (2013.01); A61F 2002/30428 (2013.01); A61F 2002/30492 (2013.01); A61F 2002/30495 (2013.01); A61F 2002/30507 (2013.01); A61F 2002/30604 (2013.01); A61F 2002/30663 (2013.01); A61F 2002/30736 (2013.01); A61F 2002/30774 (2013.01); A61F 2002/30878 (2013.01); A61F 2002/30884 (2013.01); A61F 2002/30934 (2013.01); A61F 2002/30975 (2013.01); A61F 2002/4085 (2013.01); A61F 2002/4641 (2013.01)

(56) References Cited

U.S. PATENT DOCUMENTS

| | | | |
|---|---|---|---|
| 2,780,223 | A | 2/1957 | Haggland |
| 3,593,709 | A | 7/1971 | Halloran |
| 4,364,382 | A | 12/1982 | Mennen |
| 4,429,690 | A | 2/1984 | Angelino-Pievani |
| 5,047,058 | A | 9/1991 | Roberts |
| 5,387,241 | A | 2/1995 | Hayes |
| 5,487,741 | A | 1/1996 | Maruyama et al. |
| 5,702,447 | A | 12/1997 | Walch |
| 5,755,800 | A | 5/1998 | O'Neil |
| 5,766,255 | A | 6/1998 | Slamin |
| 5,984,969 | A | 11/1999 | Matthews |
| 6,005,018 | A | 12/1999 | Cicierega |
| 6,093,188 | A | 7/2000 | Murray |
| 6,200,321 | B1 | 3/2001 | Orbay et al. |
| 6,228,119 | B1 | 5/2001 | Ondrla |
| 6,273,892 | B1 | 8/2001 | Orbay et al. |
| 6,364,881 | B1 | 4/2002 | Apgar et al. |
| 6,406,495 | B1 | 6/2002 | Schoch |
| 6,514,287 | B2 | 2/2003 | Ondrla |
| 6,699,289 | B2 | 3/2004 | Iannotti |
| 6,953,478 | B2 | 10/2005 | Bouttens |
| 7,169,184 | B2 | 1/2007 | Dalla Pria |
| 7,204,854 | B2 | 4/2007 | Guederian |
| 7,235,106 | B2 | 6/2007 | Daniels et al. |
| 7,329,284 | B2 | 2/2008 | Maroney |
| 7,445,638 | B2 | 11/2008 | Beguin et al. |
| 7,604,665 | B2 | 10/2009 | Iannotti |
| 7,608,109 | B2 | 10/2009 | Dalla Pria |
| 7,611,539 | B2 | 11/2009 | Bouttens |
| 7,753,959 | B2 | 7/2010 | Berelsman |
| 7,892,287 | B2 | 2/2011 | Deffenbaugh |
| 7,896,886 | B2 | 3/2011 | Orbay et al. |
| 7,922,769 | B2 | 4/2011 | Deffenbaugh |
| 8,007,538 | B2 | 8/2011 | Gunther |
| 8,048,165 | B2 | 11/2011 | Isch |
| 2004/0162619 | A1 | 8/2004 | Blaylock |
| 2005/0049709 | A1 | 3/2005 | Tornier |
| 2005/0060039 | A1 | 3/2005 | Cyprien |
| 2005/0192578 | A1 | 9/2005 | Horst |
| 2005/0261775 | A1 | 11/2005 | Baum |
| 2005/0278030 | A1 | 12/2005 | Tornier |
| 2006/0074430 | A1 | 4/2006 | Deffenbaugh et al. |
| 2006/0200248 | A1 | 9/2006 | Beguin |
| 2006/0235407 | A1 | 10/2006 | Wang et al. |
| 2006/0276905 | A1 | 12/2006 | Calamel |
| 2007/0021838 | A1 | 1/2007 | Dugas |
| 2007/0038302 | A1 | 2/2007 | Shultz |
| 2007/0055380 | A1 | 3/2007 | Berelsman |
| 2007/0142917 | A1 | 6/2007 | Roche |
| 2007/0156246 | A1 | 7/2007 | Meswania |
| 2007/0179624 | A1 | 8/2007 | Stone |
| 2007/0225817 | A1 | 9/2007 | Reubelt |
| 2007/0244563 | A1 | 10/2007 | Roche |
| 2007/0260321 | A1 | 11/2007 | Stchur |
| 2007/0270855 | A1 | 11/2007 | Partin |
| 2008/0015589 | A1 | 1/2008 | Hack |
| 2008/0109000 | A1 | 5/2008 | Maroney |
| 2008/0208348 | A1 | 8/2008 | Fitz |
| 2008/0243191 | A1 | 10/2008 | Tipirneni et al. |
| 2009/0149961 | A1 | 6/2009 | Dallmann |
| 2009/0164021 | A1 | 6/2009 | Dallmann |
| 2009/0192621 | A1 | 7/2009 | Winslow |
| 2009/0281630 | A1 | 11/2009 | Delince |
| 2009/0292364 | A1 | 11/2009 | Linares |
| 2010/0069966 | A1 | 3/2010 | Castaneda et al. |
| 2010/0070044 | A1 | 3/2010 | Maroney |
| 2010/0114326 | A1 | 5/2010 | Winslow |
| 2010/0125336 | A1 | 5/2010 | Johnson |
| 2010/0129138 | A1 | 5/2010 | Lariviere |
| 2010/0161065 | A1 | 6/2010 | Williams, Jr. |
| 2010/0161066 | A1 | 6/2010 | Iannotti |
| 2010/0217328 | A1 | 8/2010 | Terrill et al. |
| 2010/0217399 | A1 | 8/2010 | Groh |
| 2010/0222886 | A1 | 9/2010 | Wiley |
| 2010/0228352 | A1 | 9/2010 | Courtney, Jr. et al. |
| 2010/0274359 | A1 | 10/2010 | Brunnarius |
| 2011/0060372 | A1 | 3/2011 | Allison |
| 2011/0106266 | A1 | 5/2011 | Schwyzer |
| 2011/0112651 | A1 | 5/2011 | Blaylock |
| 2011/0137424 | A1 | 6/2011 | Lappin |
| 2011/0144758 | A1 | 6/2011 | Deffenbaugh |
| 2011/0152946 | A1 | 6/2011 | Frigg et al. |
| 2013/0090695 | A1 | 4/2013 | Bernstein et al. |

FOREIGN PATENT DOCUMENTS

| | | |
|---|---|---|
| EP | 0339530 | 11/1989 |
| EP | 1488764 A1 | 12/2004 |
| EP | 1607067 A1 | 12/2005 |
| EP | 1782764 A2 | 5/2007 |
| EP | WO2007134691 | 11/2007 |
| EP | 1656910 | 9/2008 |
| EP | 1980221 | 10/2008 |
| FR | 2855743 A1 | 12/2004 |
| WO | WO9309733 | 5/1993 |
| WO | WO2008040408 | 4/2008 |
| WO | WO 2009/092830 A1 | 7/2009 |
| WO | WO 2009/100310 A1 | 8/2009 |

OTHER PUBLICATIONS

Jones, Geary C.; In-Vitro Evaluation of ta Polyurethane Compliant LA, Proc. IMechE vol. 224 Part H: J. Engineering in Medicine (2010) pp. 551-563.

Kasten, P.; Mid-Term Survivorship Analysis of a shoulder Replacement with a Keeled Glenoid and a Modern Cementing Technique, Journal of Bone and Joint Surgery (BR) Mar. 2010 vol. 92-B, No. 387-392.

Sharma, Gulshan B.; Effect of Glenoid Prosthesis Design on Glenoid Bone Remodeling: Adaptive Finite Element based Simulation. Journal of Biomechanics 43(2010) 1653-1659.

Throckmorton, Thomas W.; Pegged Versus Keeled Glenoid Components in Total Shoulder Arthroplasty, Journal of Shoulder and Elbow Surgery (2010) 19, 726-733.

International Preliminary Report on Patentability and Written Opinion for International Application No. PCT/US2012/024035, dated Jun. 10, 2014 (6 pages).

International Preliminary Report on Patentability and Written Opinion for International Application No. PCT/US2012/068605, dated Jun. 10, 2014 (6 pages).

International Search Report for International Application No. PCT/US2012/024035, dated Aug. 7, 2012 (2 pages).

International Search Report for International Application No. PCT/US2012/068605, dated Mar. 20, 2013 (3 pages).

Patent Examination Report No. 1 for Australian Application No. 2012321087, dated Mar. 21, 2014 (3 pages).

Patent Examination Report No. 1 for Australian Application No. 2012321093, dated Feb. 26, 2014 (3 pages).

Patent Examination Report No. 2 for Australian Application No. 2012321093, dated Apr. 11, 2015 (3 pages).

GLENOID VAULT FIXATION

CROSS REFERENCE TO RELATED APPLICATIONS

This application claims the benefit of the following, which is incorporated herein by reference:

Pending prior U.S. Provisional Patent Application No. 61/568,530 filed Dec. 8, 2011, which carries Applicants', and is entitled GLENOID VAULT FIXATION.

BACKGROUND

The present disclosure relates to shoulder repair and revision surgery. More accurately, the present disclosure relates to a shoulder prosthetic and more precisely to a glenoid or glenosphere vault system for repairing or revising a shoulder. It is contemplated that this system is applicable to shoulder and reverse shoulder repair. It is contemplated that the systems and methods set forth herein, or any adaptations, may be useful outside of and beyond shoulder repair and humerus repair.

One attribute of shoulder repair surgery is the limit of anatomical bone the patient has to provide for adequate repair and even more so with shoulder revision. The shoulder naturally only provides a limited amount of bone for the shoulder joint to function. When shoulder repair is needed it is often performed with large anchor devices embedded in what bone is available to allow for proper security of an articulating surface or glenosphere to attach to the anchor. These devices require a large removal of bone. Further revision surgery requires even greater bone loss as original anchors are removed and replaced with new anchors. There is a need to have a smaller footprint anchor without limiting the fixation of the articulating components. There is also a need to have the ability for revision shoulder repair without removal of the original anchors, solely replacing the articulating components.

BRIEF DESCRIPTION OF THE DRAWINGS

Various embodiments of the present system will now be discussed with reference to the appended drawings. It is appreciated that these drawings depict only typical examples of the present system and are therefore not to be considered limiting of the scope of the invention, as set forth in the appended claims.

DETAILED DESCRIPTION

The present disclosure provides systems, apparatus, and methods for shoulder replacement, repair and revision. The systems and methods described herein may improve shoulder prosthetics for use in shoulder arthoplasty and revision surgeries and provide stronger attachment of prosthetics to bone.

In this specification, standard medical directional terms are employed with their ordinary and customary meanings. Superior means toward the head. Inferior means away from the head. Anterior means toward the front. Posterior means toward the back. Medial means toward the midline, or plane of bilateral symmetry, of the body. Lateral means away from the midline of the body. Proximal means toward the trunk of the body. Distal means away from the trunk.

In this specification, standard shoulder anatomical terms are employed with their ordinary and customary meanings.

Figure 1:
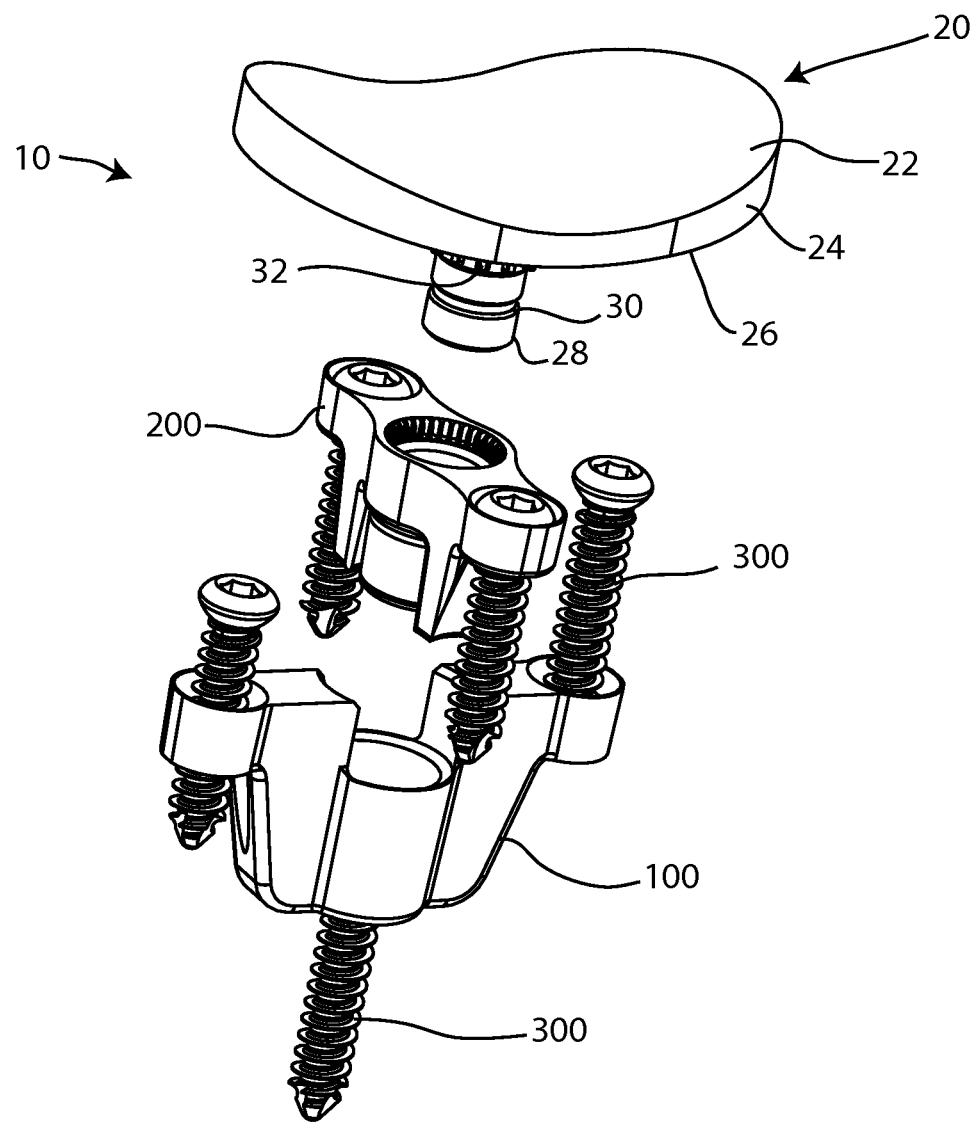
FIG. 1 is an exploded perspective view of a glenoid vault system with a superior-inferior (SI) component, an anterior-posterior (AP) component, an articulating component and screws.

Referring to FIG. 1, a perspective view illustrates a glenoid vault system 10 that may be implanted into a shoulder. The glenoid vault system 10 includes an articulating component 20, anchoring components with include a superior-inferior (SI) or vertical component 100, an anterior-posterior (AP) or horizontal component 200 and anchors 300 which may be screws. The system 10 allows interaction of the different components with the articulating component 20 engaging the AP component 200 and the AP component engaging the SI component 100. The screws 300 may pass through different portions of the AP component 200 and the SI component 100.

The articulating component 20 has a curvature shaped to mirror an anatomical shoulder with a semi-spherical or concave articulating surface 22 peripherally surrounded by a wall 24. The articulating component also includes a bone-facing surface 26 facing the opposite direction as the articulating surface 22 and a post 28 extending from the bone-facing surface 26 in a substantially central location of the bone-facing surface 26. The post 28 may also extend substantially perpendicular to the articulating surface 22. The bone facing surface 26 may rest against the shoulder bone. The post 28 may include a ring shaped cutout 30 toward the distal end of the post 28 and notches 32 toward the proximal end of the post 28.

Figure 2:
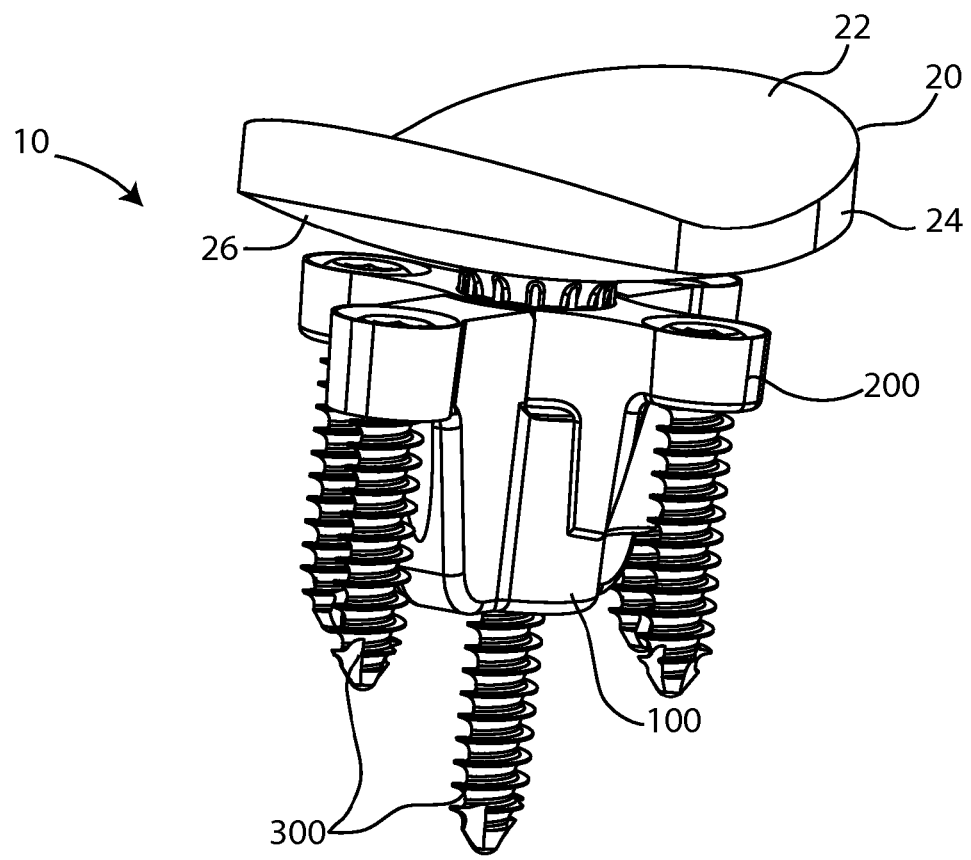
FIG. 2 is an assembled perspective view of the glenoid vault system of FIG. 1.
Figure 3:
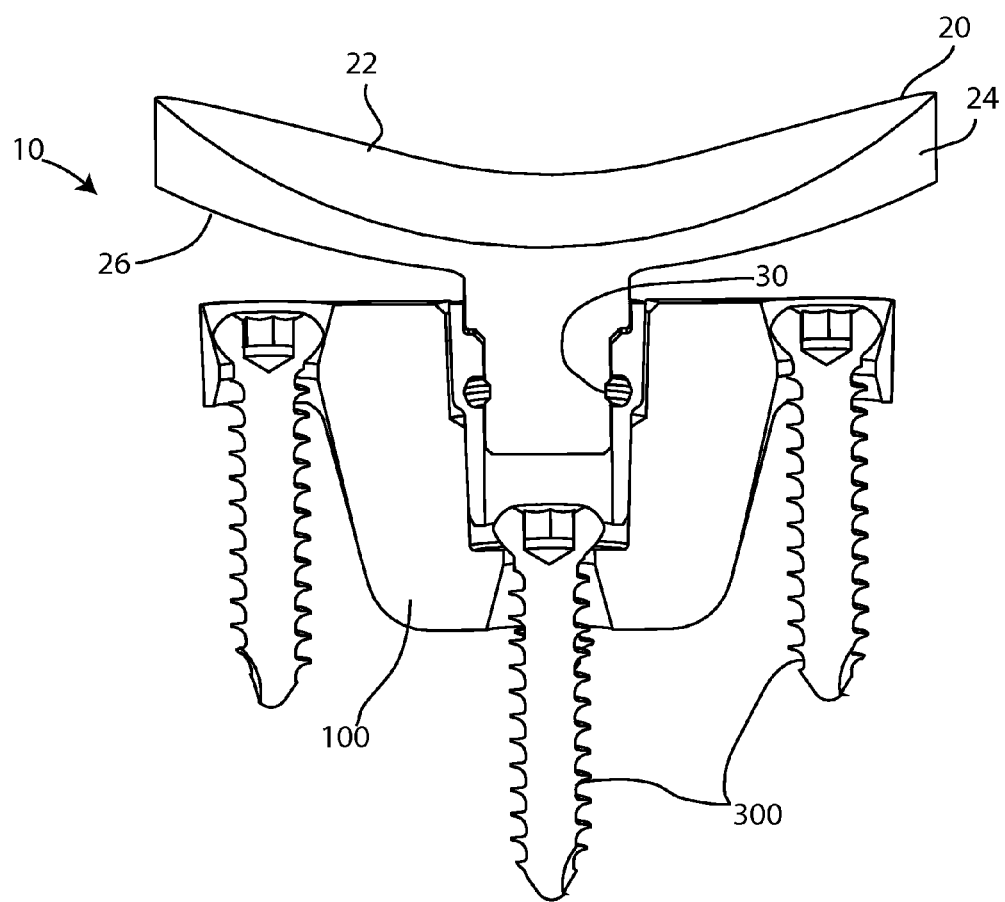
FIG. 3 is a cross sectional side view of the glenoid vault system of FIG. 1.
Figure 4:
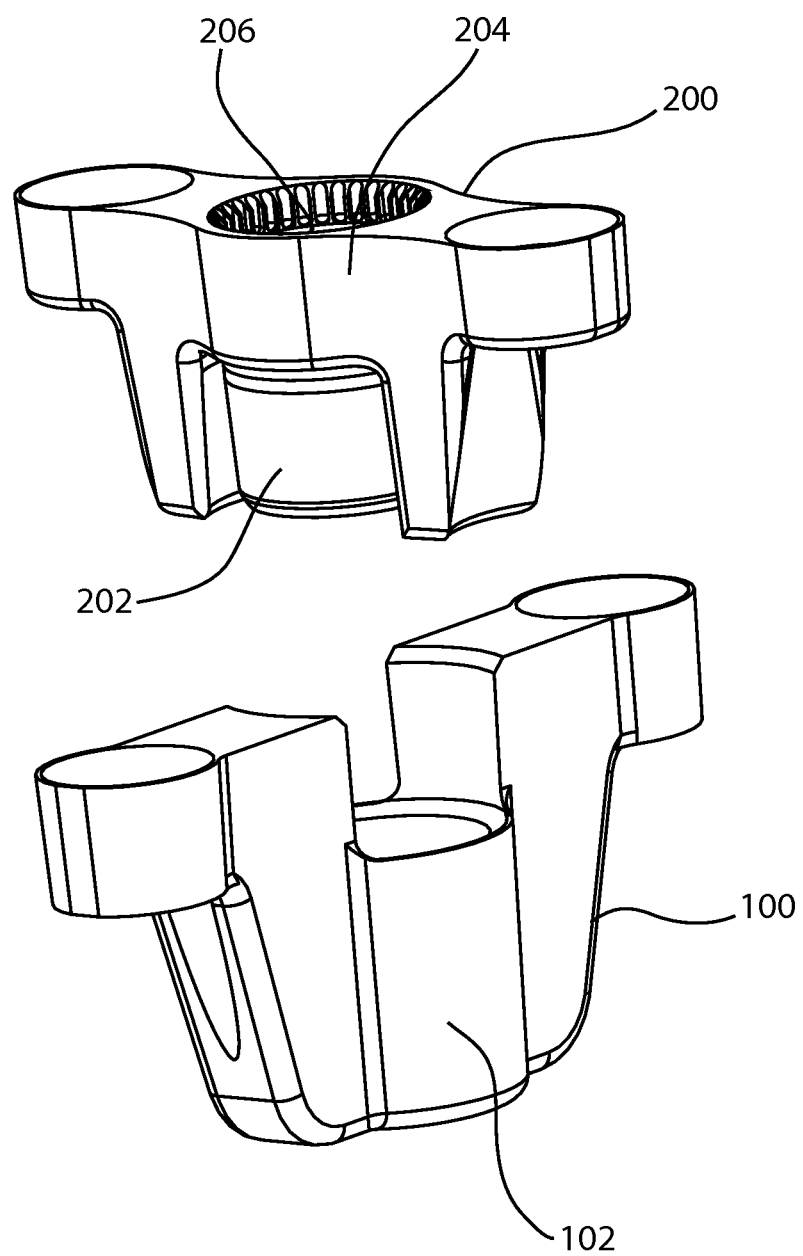
FIG. 4 is an exploded perspective view of the SI and AP components of FIG. 1.
Figure 5:
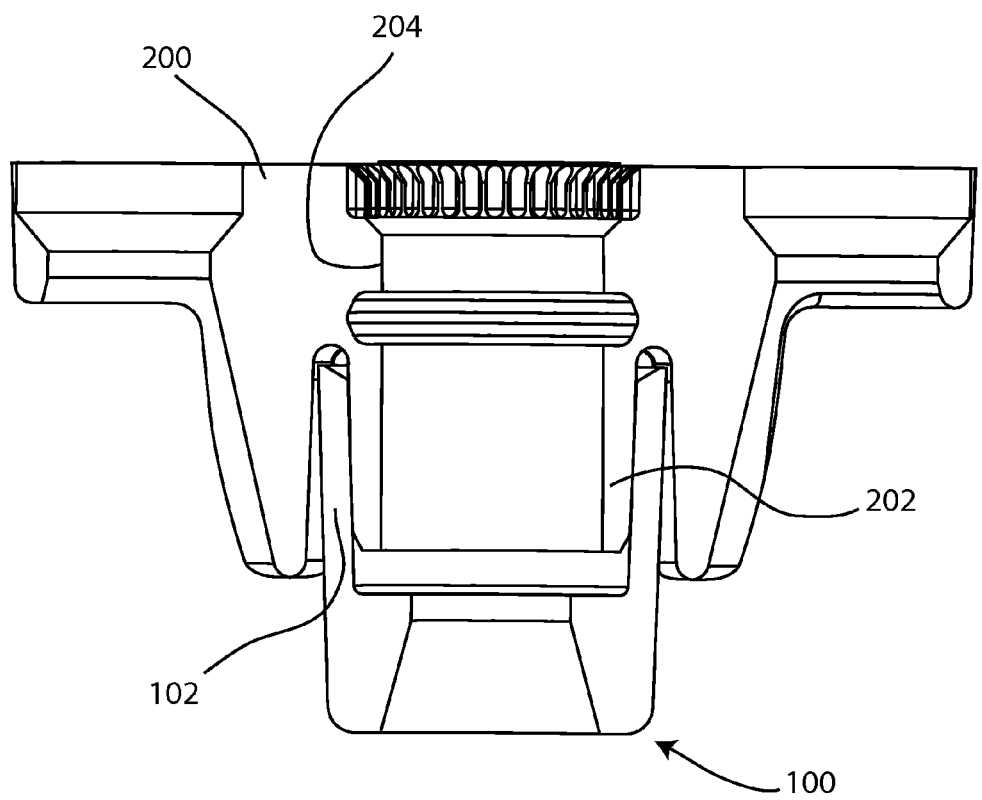
FIG. 5 is a cross-sectional side view of the assembled SI and AP components of FIG. 1.
Figure 6:
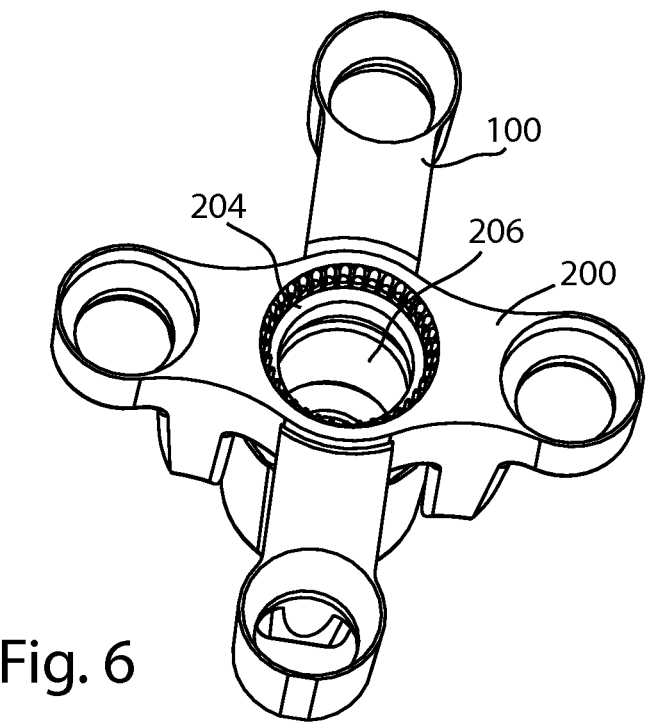
FIG. 6 is a perspective top view of the SI and AP components of FIG. 1.
Figure 7:
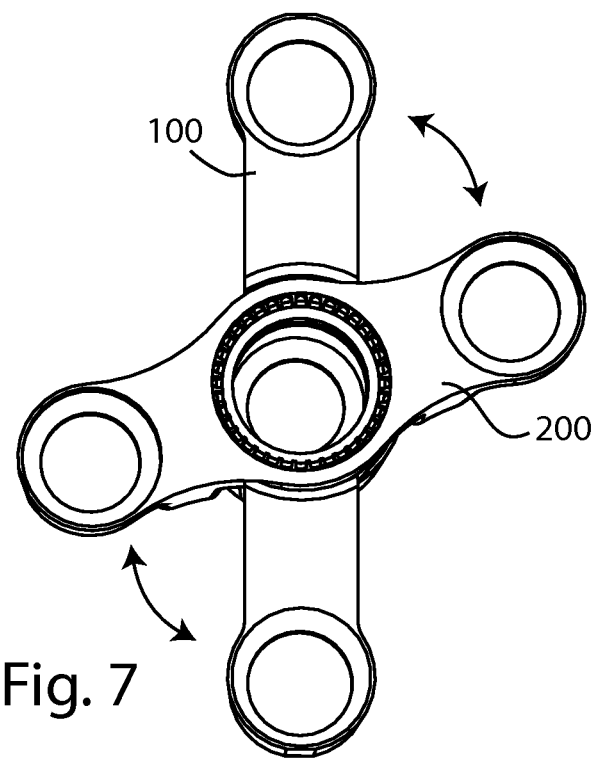
FIG. 7 is a top view of the SI and AP components of FIG. 1 with the AP component rotated to show it is rotatable about the center of the SI component.

Referring to FIGS. 2 and 3, the glenoid vault system 10 assembles with the SI component 100 being embedded in the bone (not shown). The AP component 200 may rotate about a portion of the SI component with at least a portion of the AP component 200 within the SI component 100 before the AP component 200 is secured to the bone. The post 28 of the articulating component 20 may engage the AP component 200 with the ring shaped cutout 30 or a ring shaped protrusion with a complimentary seal or snap fit, or other locking means including a Morse taper (not shown) which may not require an engagement ring, on the AP component 200. The system is described in further detail herein.

Referring to FIGS. 4-7, the SI component 100 and AP component 200 interact through a body 102, which may be a central ring, of the SI component 100 and a tubular boss 202 of the AP component 200. The body 102 may be a ring and the ring may be central to the SI component 100; however, the geometric component may be offset from the center as well and may be any shape including cylindrical or other polygonal shape. The tubular boss 202 extends distally from a cylindrical wall 204 defining a hole 206, wherein the hole may be a centralized or a central hole. The tubular boss 202 may slidably engage the central ring 102 allowing the AP component 200 to rotate about the central ring 102 of the SI component 100. The AP component 200 may be secured to the SI component 100 through a Morse taper. The SI and AP components 100, 200 form a cruciate when they are engaged. A cruciate means a cross shape or X shape.

Figure 8:
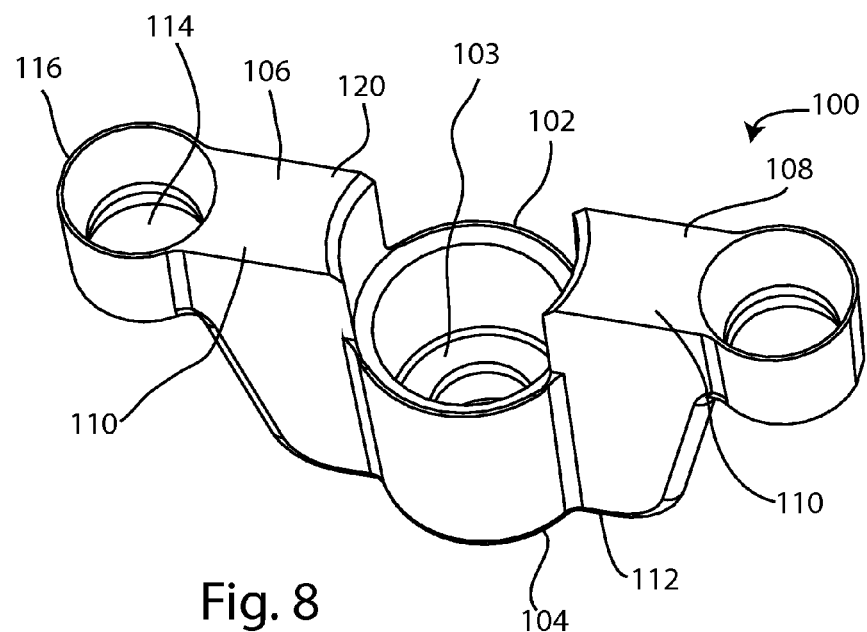
FIG. 8 is a perspective view of the SI component of FIG. 1.

Referring to FIG. 8, the SI component 100 may include a bore 103, which may be a central bore, extending at least partially through the body or central ring 102 in a longitudinal direction and may extend entirely through the central ring 102. The SI component includes a distal end 104 and may include two arms 106, 108 extending from the central ring 102. The arms 106, 108 include a proximal end 110 and a distal end 112 that is the same distal end 112, 104 of the SI component 100. Portions of the arms 106, 108 extend proximally from the central ring 102 giving the SI component 100 a V or U-shaped configuration for the SI component 100. The extension of the arms 106 proximally may be substantially parallel and substantially the same length, wherein the arms are coplanar; however the arms may differ in length slightly as well which may give the SI component 100 a J-shape, wherein the arms are not coplanar. The extension of the arms 106, 108 may be collinear and the arms 106, 108 may prove to be mirror images if a cross section is taken of the SI component 100. The portion of the arms 106, 108 toward the central ring 102 may cylindrically curve around the central ring 102 with the same degree of curvature as the central ring 102. The body of the SI component 100 may be longer than it is wide from a top view providing a narrow footprint when the SI component sits within the bone with the arms 106, 108 narrower than the central ring 102.

Figure 9:
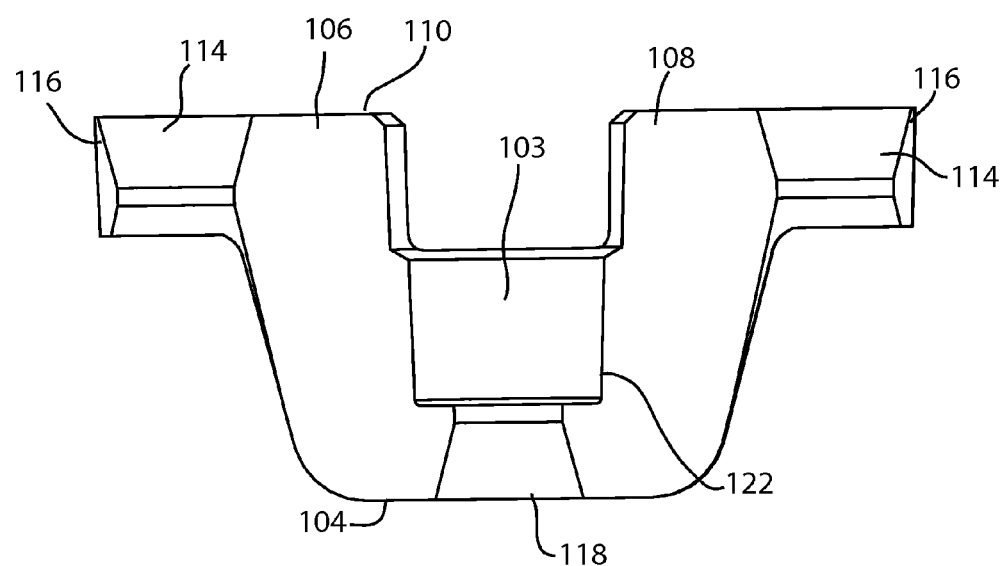
FIG. 9 is a cross-sectional side view of the SI component of FIG. 1.

The arm 106 may include an opening or bore 114 defined by a wall 116, which may be an arm ring, which may be cylindrical in shape, at the end of the arm 106. Bores 114 may also be referred to as lateral passages. The arm ring 116 may protrude from the arm 106 in substantially the same direction as the arm 106 extending from the central ring 102. The opening 114 may extend entirely through the arm ring 116 substantially parallel with the central bore 103. The opening 114 is substantially circular in cross section and configured to receive a screw 300. The opening 114 may include recesses, conical in shape, to guide the screw 300 into place in the SI component 100 as well as seat the screw 300 in its proper place. The opening 114 may be a double conical shape with the narrowest point seated toward the middle of the opening 114, the shape expanding outward toward either end of opening 114, as best seen in FIG. 9. The opening 114 may slidably or threadably receive the screws 300. The recesses in the openings 114 may allow for the heads of the screws 300 to sit flush with a proximal surface 120 at the proximal end 110 of the arms 106, 108 of the SI component 100. The arm 108 may include similar or identical features as arm 106, but extending in the opposite direction from the central ring 102.

The SI component 100 may be made from numerous different materials that include, but should not be limited to, titanium and alloys, cobalt-chrome and alloys, stainless steel, ceramic, tantalum, PEEK, PEAK, hydroxyapatite and biocompatible materials.

Referring to FIG. 9, the central ring 102 includes a larger cylindrical receiver 122 for receiving the tubular boss 202 of the AP component 200. The central ring 102 also includes a central opening 118 distal the cylindrical receiver 122. The central opening 118 may be conical in shape with the wider portion of the central opening toward the distal end 104. One screw 300 may pass through the central bore 103, the head of the screw engaging the SI component 100 and locking it to the bone. The screw 300 may threadably or slidably engage the central bore 103.

A bone, wherein the bone may be a scapula, may be properly prepared by placing a guidewire on the bone. The bone is then reamed and a primary hole is drilled, the primary hole is drilled at size to allow the central ring 102 of the SI component 100 to fit within the primary hole. Secondary holes or pilot are drilled, sized, and shaped to accept other portions of the SI component. A cutting or punch instrument may be used to connect or bridge the primary and secondary holes. The bone is then broached for the near net shape of the SI component 100. An SI broach may be used as a trial implant. With the broach in the bone, or vault of the bone, the AP holes may be drilled to fit the exact size of the AP component 200. The same steps for the preparation of the SI component 100 are mimicked for the AP component 200 while the SI trial is in the bone, or vault of the bone. After proper size, shape and orientation are determined, the AP and SI trials are removed and replaced with the actual SI and AP components 100, 200, that can be secured to the bone using proper screws 300 or other anchors. The screws 300 may through the central bore 103 and the head of the screw 300 engages the SI component 100 through the conical shaped opening, securing the SI component to the bone. Additional screws may pass through the openings 114 for greater security of the SI component 100 to the bone. The AP component 200 may be further secured as well with screws that pass through holes 214 of the AP component 200.

Figure 10:
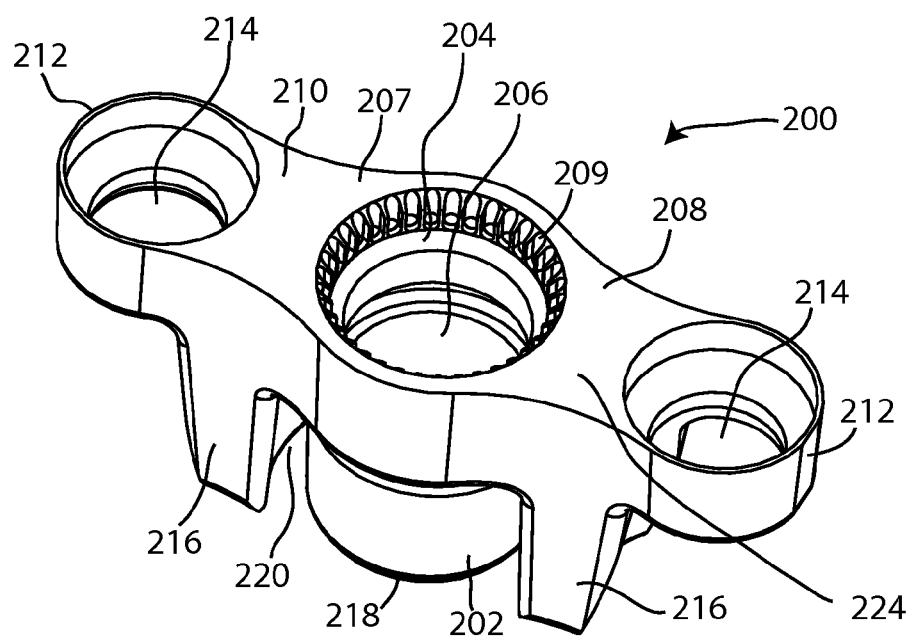
FIG. 10 is a perspective view of the AP component of FIG. 1.
Figure 11:
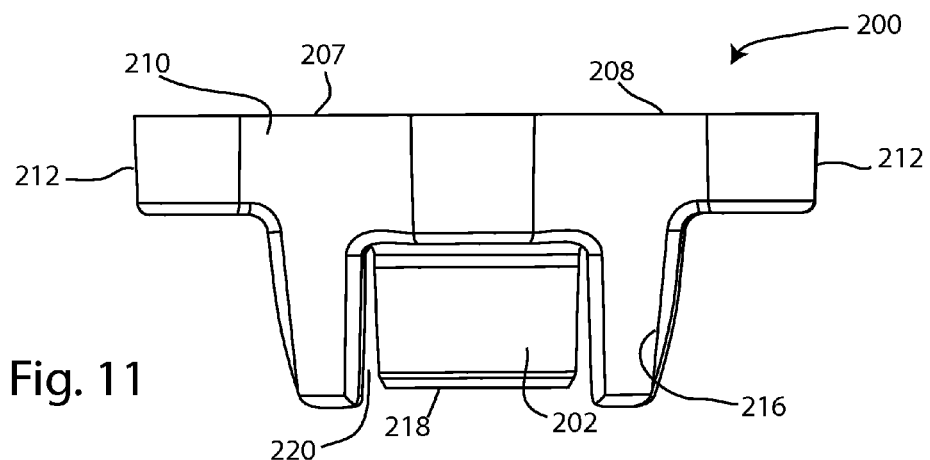
FIG. 11 is a side view of the AP component of FIG. 1.

Referring to FIGS. 10 and 11, the AP component 200 may include the central cylindrical wall 204 defining the central hole 206 extending entirely through the AP component with the central hole 206 passing into the tubular boss 202. The tube of the tubular boss 202 may be an extension of the central hole 206. The tubular boss 202 may be circumferentially smaller than the cylindrical wall 204 defining the central hole 206. At a proximal end 207 of the central hole 206 of the AP component 200 may reside notches or grooves 209 that allow rotational orientation of the articulating component 20 and may serve as a keyed or complimentary fit with the articulating component 20 to prevent rotation of the articulating component 20 after engaging the AP component 200. The notches or grooves 209 may be cross sectionally rounded or squared or any other shape to prevent rotation of the articulating component 20 after engaging the AP component 200.

An alternate embodiment of an anti-rotation/rotational orientation feature which may take the place of the notches or grooves 209 may include splines (not shown) extending from a proximal surface 224 of either the AP or SI component 100, 200. The splines may engage crescent bosses (not shown) that extend from the bone facing surface 26 of the articulating component 20. The crescent bosses may include multiple holes for receiving the splines.

First and second AP arms 208, 210 extend away from the central hole 206 at or toward the proximal end 207 of the AP component 200. The AP arms 208, 210 may be collinear with the first AP arm 208 extending in an opposite direction as the second AP arm 210. Each of the AP arms 208, 210 may be the same length; however, the AP arms 208, 210 may differ in length as well depending on the patient anatomy and what bone is available to secure the AP component 200 to. Similar to the SI component arms 106, 108 the AP arms 208, 210 each have arm walls 212, which may be AP arm rings. The AP arm rings 212 may protrude from the arms 208, 210 in substantially the same direction as the arms 208, 210 extending from the cylindrical wall 204. The AP arm rings 212 include holes 214 extending entirely through the AP arm rings. The holes 214 may also be referred to as AP lateral passages. The holes 214 may be substantially cylindrical in shape, to allow for passage of the screws 300 to aid in securing the AP component 200 to the bone.

One or more keels 216 may extend distally from the AP arms toward a distal end 218 of the tubular boss 202. The keels 216 may be used for bone purchase. The keels 216 may extend beyond the distal end 218 of the tubular boss keels 216 may cylindrically curve around the tubular boss 202 with the same degree of curvature as the tubular boss 202. The keels 216 may extend substantially parallel to one another creating a slot 220 between each one of the keels 216 and the tubular boss 202. The slot 220 receives the central ring 102 of the SI component 100. The keels 216 may provide rotational stops when the keels engage the arms 106, 108 of the SI component 100 preventing any further rotations of the AP component 200. The body of the AP component 200 may be longer than it is wide providing a narrow footprint when the AP component 200 engages the SI component 100 and resides in the bone.

Figure 12:
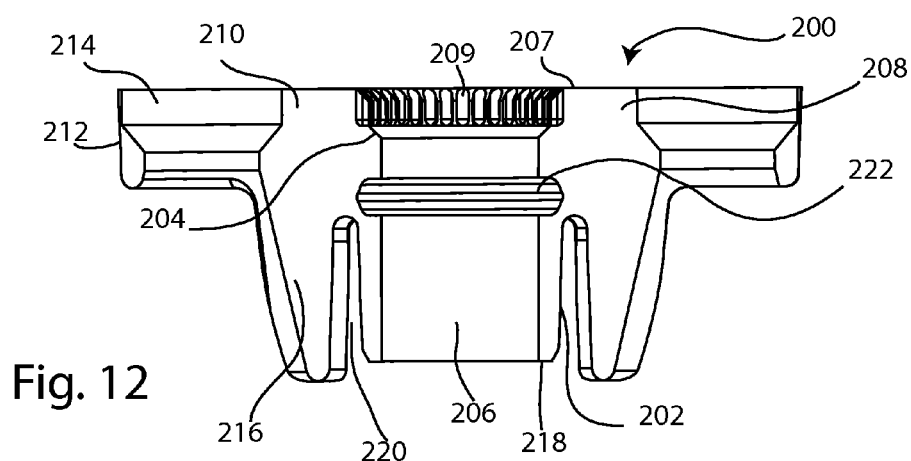
FIG. 12 is a cross-sectional side view of the AP component of FIG. 1.

Referring to FIG. 12, an engagement ring 222 is positioned on the central wall 204 within the central hole 206 of the AP component 100. The engagement ring 222 is positioned toward the proximal end of the AP component end but distal to the notches or grooves 209. The engagement ring may protrude out from the central wall 204, extend toward the center of the central hole 206, or it may be a cut out within the central wall 204, extending away from the center of the central hole 206. The engagement ring 222 serves to engage and reversibly lock axial movement the ring shaped cutout 30 or protrusion of the post 28 of the articulating member 20 to the AP component 200. The post 28 of the articulating component 20 includes a complimentary fit with the engagement ring 222 whether it is a protrusive ring or cut out ring. The complimentary fit between the ring shaped cutout 30 and the engagement ring 222 may be a snap fit or seal or any other means for reversibly locking the articulating component 20 to the AP component 200, including a Morse taper (not shown) which may not require an engagement ring.

The holes 214 in the arms 208, 210 may taper or recess from the proximal end 207 toward a distal end providing guidance for the screws and engagement with the screw heads. The holes 214 may threadably or slidably receive the screws 300 and the recesses or tapers may allow the screw head to sit flush with a proximal surface 224 at the proximal end 207 of the AP component 200.

The AP component 200 may be made from numerous different materials, which include, but should not be limited to, titanium and alloys, cobalt-chrome and alloys, stainless steel, ceramic, tantalum, hydroxyapatite and biocompatible materials.

One method of implanting the system 10 includes preparing the bone as Previously described and implanting the SI component 100 into the bone with appropriate screws 300. The AP component 200 may properly engage the SI component 100 with the tubular boss 202 slidably engaging the central ring 102, the tubular boss 202 sliding within the central ring 102. The AP component 200 is carefully placed at a proper angle, which may be predetermined, within the best available bone to provide greater security. Screws 300 may pass through the holes 214 to secure the AP component 200 to the bone. The articulating component 20 may engage the AP component 200 after the AP component 200 is properly placed and positioned within the SI component 100 and the bone. The order in which the components engage one another is not restrictive and a separate order may be established such as engaging the SI and AP component 100, 200 prior to implanting into the bone.

Figure 13:
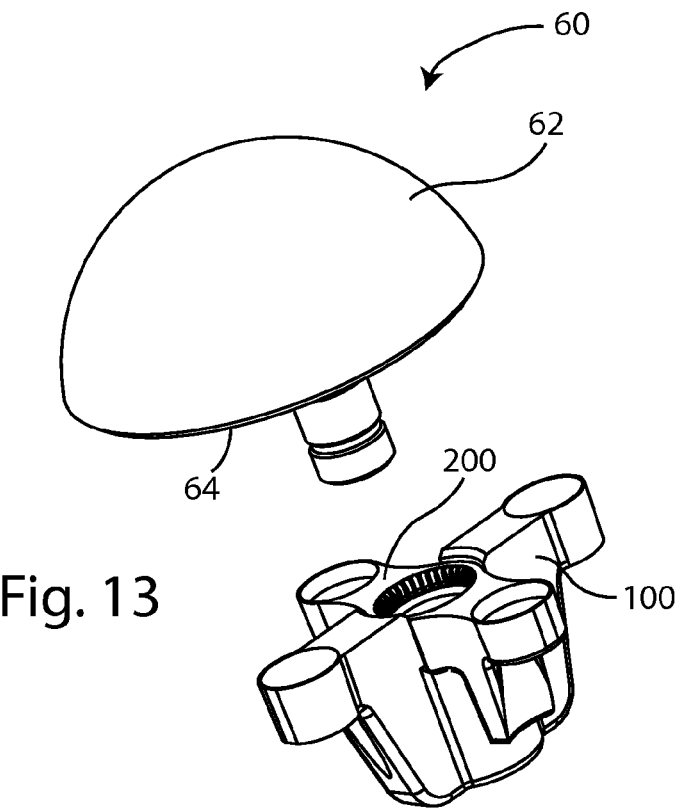
FIG. 13 is a partially exploded perspective view of the SI and AP components of FIG. 1 and a glenosphere.
Figure 14:
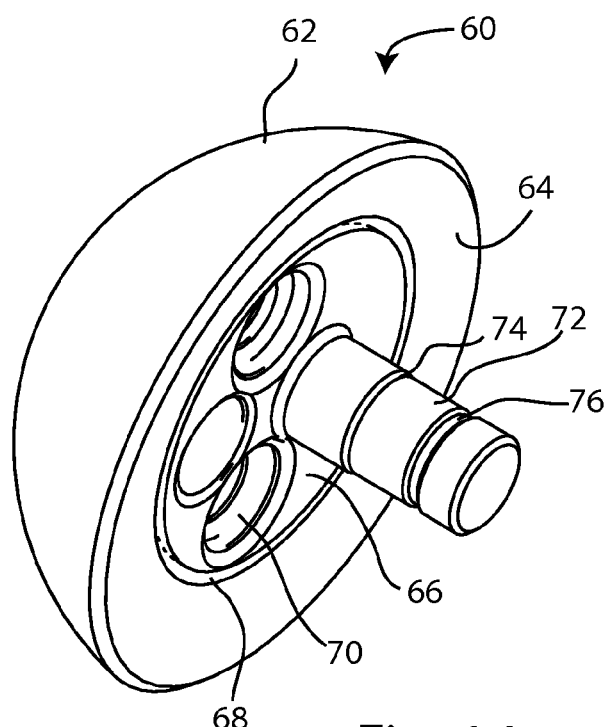
FIG. 14 is a bottom perspective view of the glenosphere of FIG. 13.

Referring to FIGS. 13 and 14, a glenosphere 60 may replace or be used instead of an articulating component 20. The glenosphere 60 may be used for a reverse shoulder arthroplasty but may engage the AP component 200 in the same manner as the articulating component 20. The glenosphere 60 may be semi-spherical or domed and include an articulating surface 62 that may comprise the semi-spherical portion of the glenosphere 60 with a bone-facing surface 64. The glenosphere 60 may also include a metaglene component 66 on the bone facing surface 64 side of the glenosphere 60. The metaglene component 66 may be a separate piece that fits within a dome cutout 68. The metaglene 66 may be stoutly cylindrical. The dome cutout 68 may be circular in cross section on the bone facing side of the semispherical portion of the glenosphere 60. The metaglene 66 engages the dome cutout 68 through a press or snap-fit sitting flush with the glenosphere bone facing surface 64. The metaglene 66 may also be a single piece with the glenosphere 60.

The metaglene 66 may include metaglene holes 70 passing through the body of The metaglene 66 that may be used to pass screws through to fixate to the metaglene 66 to bone. The metaglene holes 70 may also provide a place for securing an augment to the glenosphere 60. A post 72 extends away from the metaglene 66 in a similar fashion as the articulating component post 28. The glenosphere post 72 may include at least one step-down 74 as well as a post cutout 76. The post cutout 76 may engage the engagement ring 222 of the AP component 200 in a manner similar to or identical to the manner of the articulating component post 28 of the articulating component 20.

The glenosphere 60 and the articulating component 20 may engage the AP component 200 without removal of either the AP component 200 or the SI component 100 of the glenoid vault system 10. Revision surgery is done with greater ease because the components can be snapped in and out of the SI and AP anchors 100, 200 without removal of any more bone.

Figure 15:
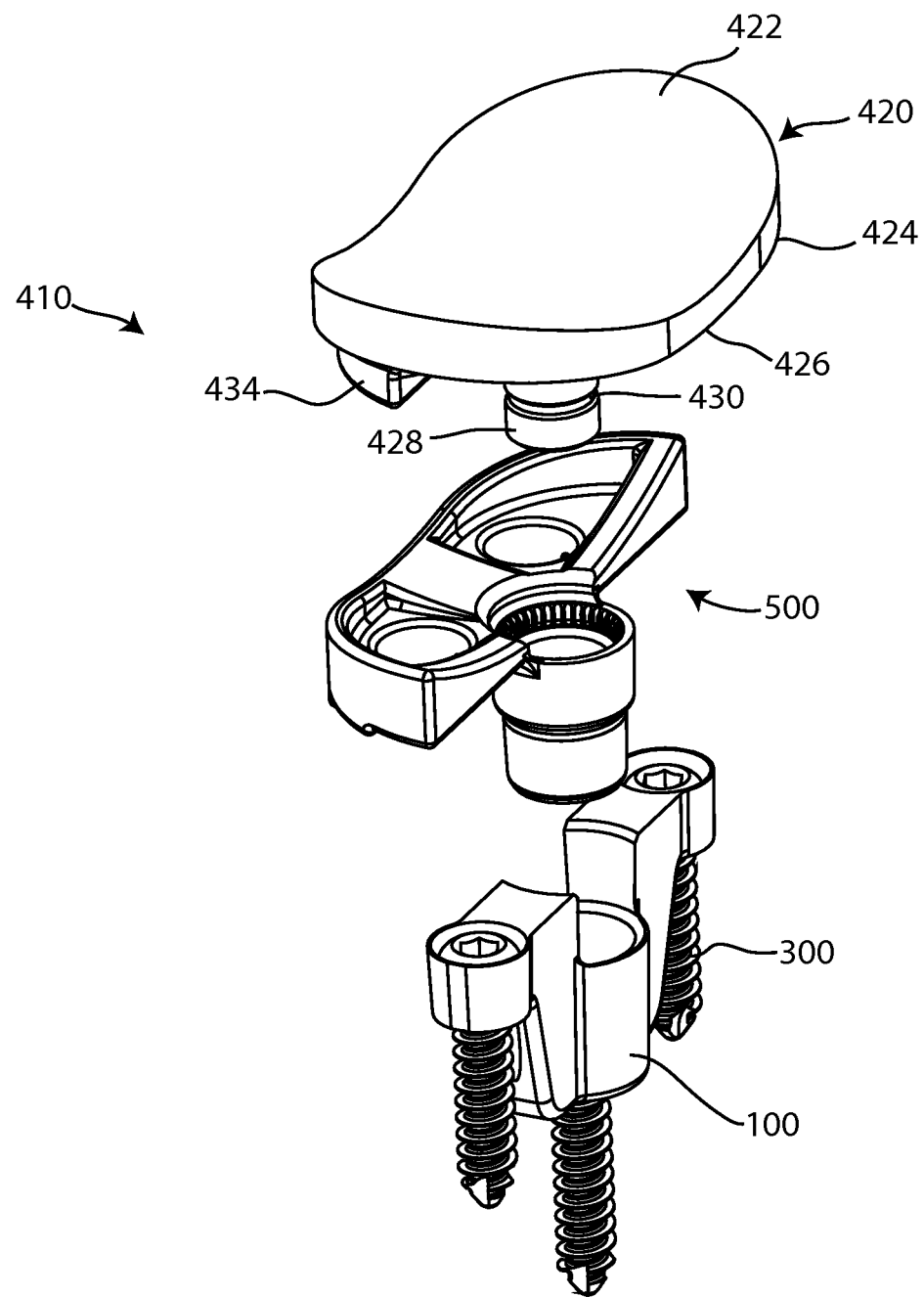
FIG. 15 is an exploded perspective view of a glenoid vault system with an SI component, an AP component with an augment, an articulating component and screws.
Figure 16:
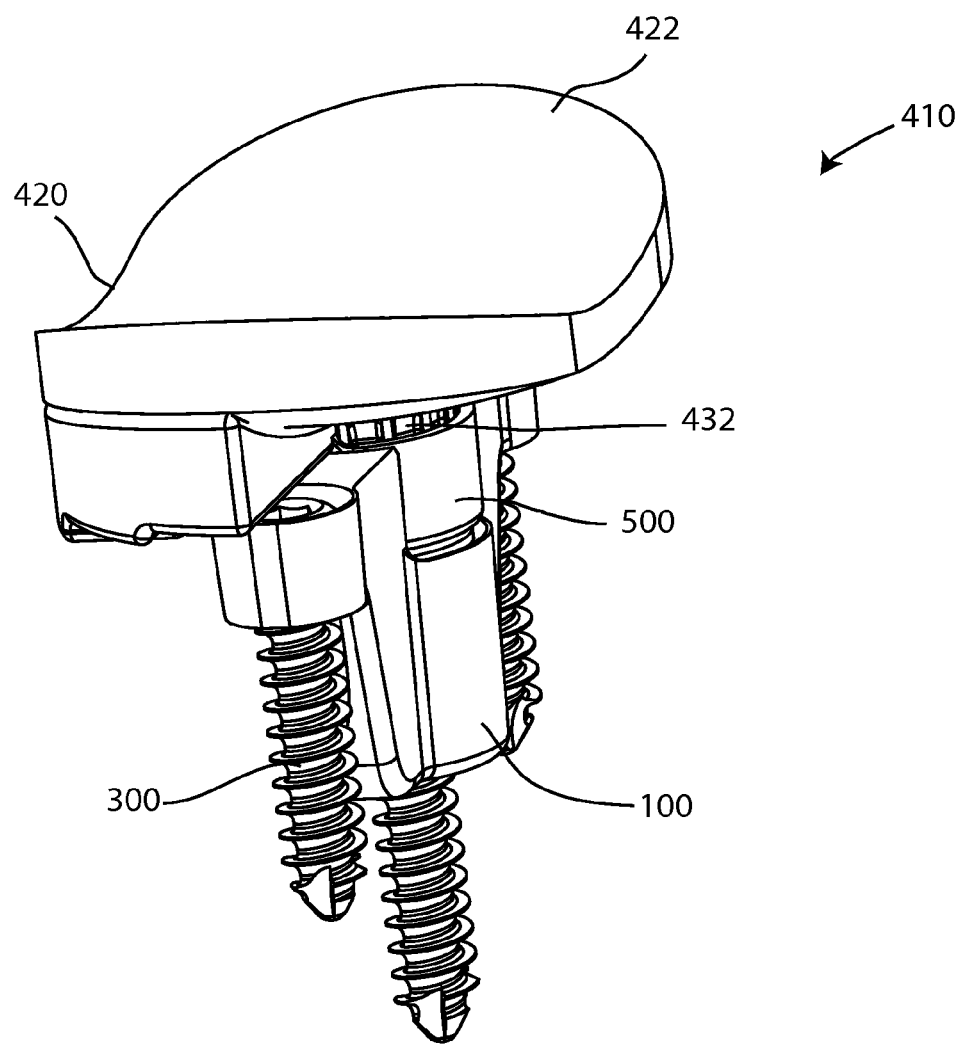
FIG. 16 is an assembled perspective view of the glenoid vault system of FIG. 15.

Referring to FIGS. 15 and 16, an alternate embodiment of a glenoid vault system 410 includes an articulating member 420, an AP component 500 with an augment, the SI component 100 and the anchors or screws 300. The interaction between the different components is similar to the previous embodiment.

The articulating member 420 is substantially similar to the previous embodiment. The articulating member 420 has a curvature shaped to mirror an anatomical shoulder with a semi-spherical or concave articulating surface 422 peripherally surrounded by a wall 424. The articulating component also includes a bone-facing surface 426 facing the opposite direction as the articulating surface 422 and a post 428 extending from the bone-facing surface 426 in a substantially central location of the bone-facing surface 426. The bone facing surface 426 may rest against the scapula. The post 428 may include a ring shaped cutout 430 toward the distal end of the post 428 and notches 432 toward the proximal end of the post 428. However, this embodiment of the articulating member 420 includes an augment 434 extending from the bone facing surface 426 separate from the post 428 and the augment 434 is not as long as the post 428. The augment 434 extends from only one side of the bone-facing surface 426 and the other portion of the bone facing surface 426 matches the curvature of the articulating surface 422. The augment 434 may match the curvature of the peripheral wall 424 and its curvature on the one side of the articulating member 420. The augment 434 interacts with a portion of the AP component 500 that will be discussed further herein. The augment 434 is provided to replace an area where much of the bone has been removed.

Figure 17:
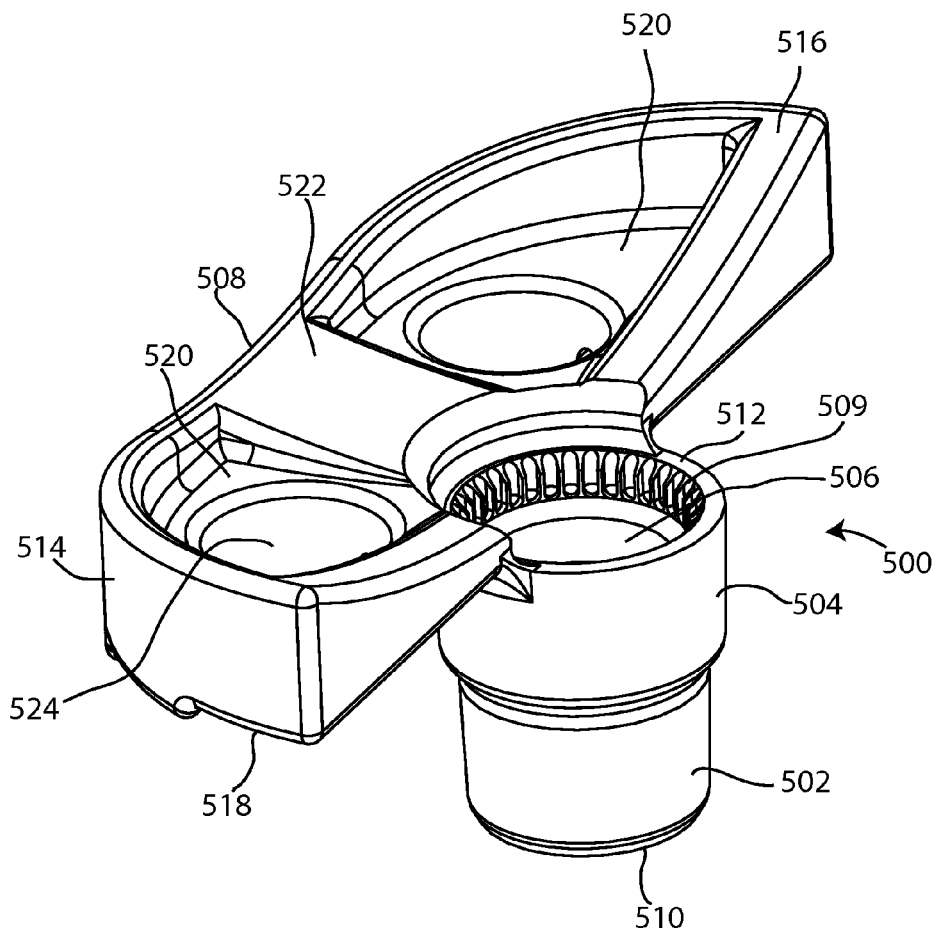
FIG. 17 is a perspective view of the AP component of FIG. 15.

Referring to FIG. 17, the AP component 500 may include the central cylindrical wall 504 defining central hole 506 extending entirely through the AP component with the central hole 506 passing into the tubular boss 502. The tube of the tubular boss 502 may be an extension of the central hole 506. The tubular boss 502 may be circumferentially smaller than the cylindrical wall 504 defining the central hole 506 while the circumference of the central hole 506 may remain constant through from the cylindrical wall 504 to a distal end 510 of the tubular boss 502. At a proximal end 512 the central hole 506 of the AP component 500 may reside notches or grooves 509 that may serve a complimentary fit with the notches 432 of the articulating component 420 to allow rotational orientation of the articulating component and prevent rotation of the articulating component 420 after engaging the AP component 500.

An AP augment 508 extends away from the central hole 506 from the distal end 510 of the AP component 500. The AP augment 508 may extend 180° or more around the circumferential edge of the cylindrical wall 504. A peripheral wall 514 wraps around the AP augment 508 and may match the curvature of the articulating member 420. The AP augment 508 also include an articulating facing side 516 and a bone facing side 518. The articulating facing side 516 may include pockets 520 divided by a ridge 522. The pockets 520 receive and complimentary fit the augment 434 of the articulating member 420. The pockets 520 may match the curvature of the peripheral wall 514 of the AP augment 508. Within each pocket 520 may include an augment hole 524 to allow for passage of a screw. The augment hole 524 may pass through the entire body of the AP augment 508 in substantially the same direction as the central hole 506. The screw may threadably or slidably pass through the augment hole 524 wherein the screw head may engage the augment hole 524 and secure the AP component 500 to the bone.

The AP component 500 may include the same or similar features as the previously described embodiment including the engagement ring 222 that engages the ring shaped cutout 430 of the articulating member 420. The AP component 500 also includes the grooves or notches 509 that interact with the notches 432 of the articulating member 420 in much the same manner as the previous embodiment to allow rotational orientation of the articulating component and prevent rotation of the articulating member 420 about the AP component 500.

A method of implanting this embodiment of the glenoid vault system 410 is similar to that previously described herein substituting the alternate embodiment AP component 500 for the previous AP component 200.

Figures 18, 19:
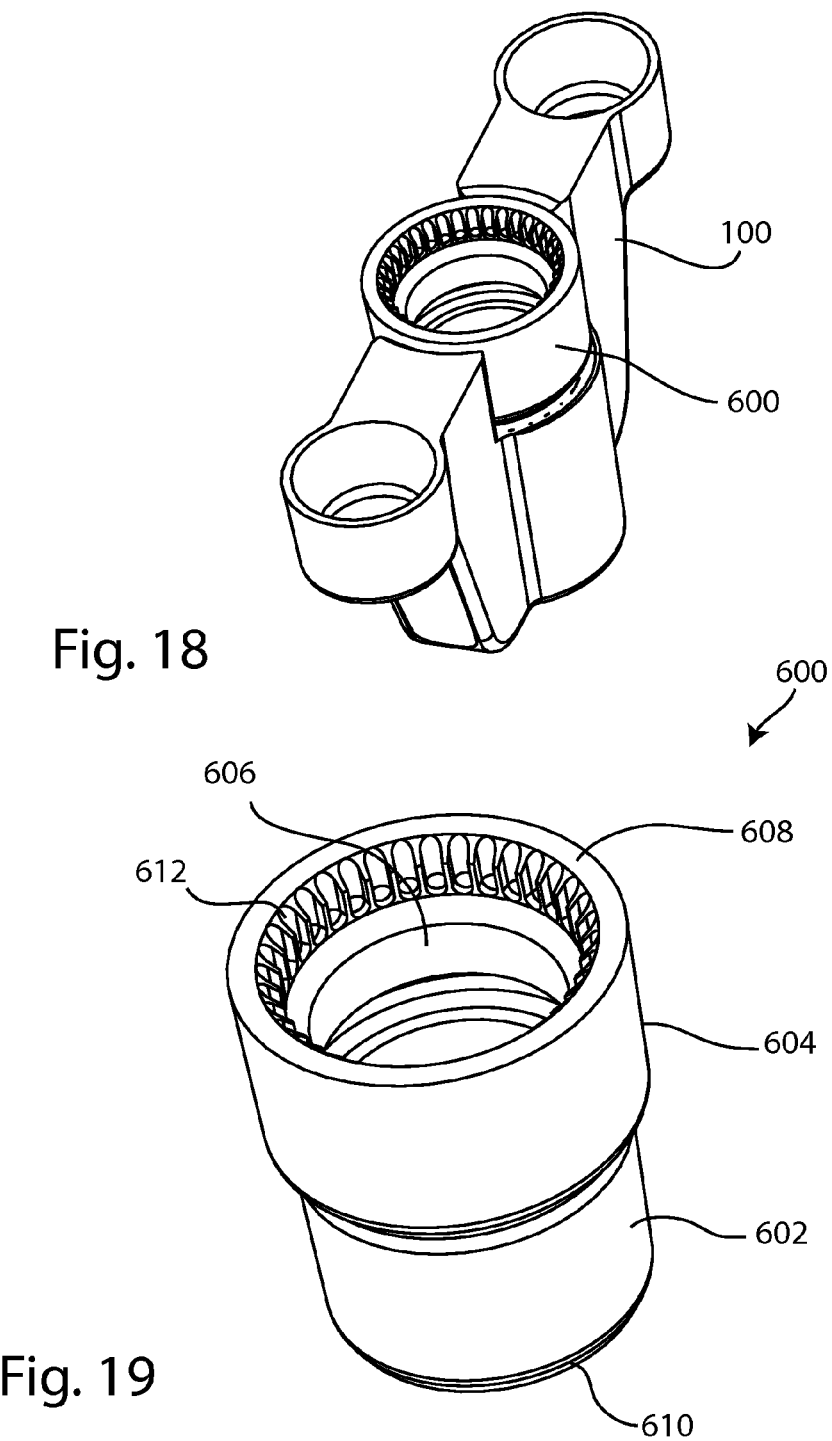
FIG. 18 is a perspective view of an assembled SI component of FIG. 1 or 15 and a cylindrical component.
FIG. 19 is a perspective view of the cylindrical component of FIG. 18.

Referring to FIGS. 18 and 19, a cylindrical component 600 may include some of the similar features of the previous AP components 200, 500. The cylindrical component 600 includes the same or similar features as the previously disclosed AP components 200, 500 with the exclusion of arms and augments and simply includes the cylindrical portion itself. Cylindrical component 600 includes a tubular boss 602 extending from a cylindrical wall 604 defining a central hole 606. The tubular boss 602 may be circumferentially smaller than the cylindrical wall 604 defining the central hole 606 while the circumference of the central hole 506 may remain constant through from a proximal end 608 of the cylindrical wall 604 to a distal end 610 of the tubular boss 602. Similar to the previous embodiments, at the proximal end 608 of the cylindrical wall 604 reside notches or grooves 612 which may serve as a complimentary fit with the notches of the articulating members or components, or the glenosphere to allow rotational orientation of the articulating component and prevent rotation of the articulating member or component, or glenosphere after engaging the AP component 600.

The cylindrical component 600 may also include the engagement ring 222 as previously disclosed for securing an articulating component or member or glenosphere, particularly the post portion of the articulating component, to the cylindrical component 600. The security of the two parts may come from a seal or snap fit, or other locking means including a Morse taper (not shown) which may not require an engagement ring, as previously described herein.

Figure 20:
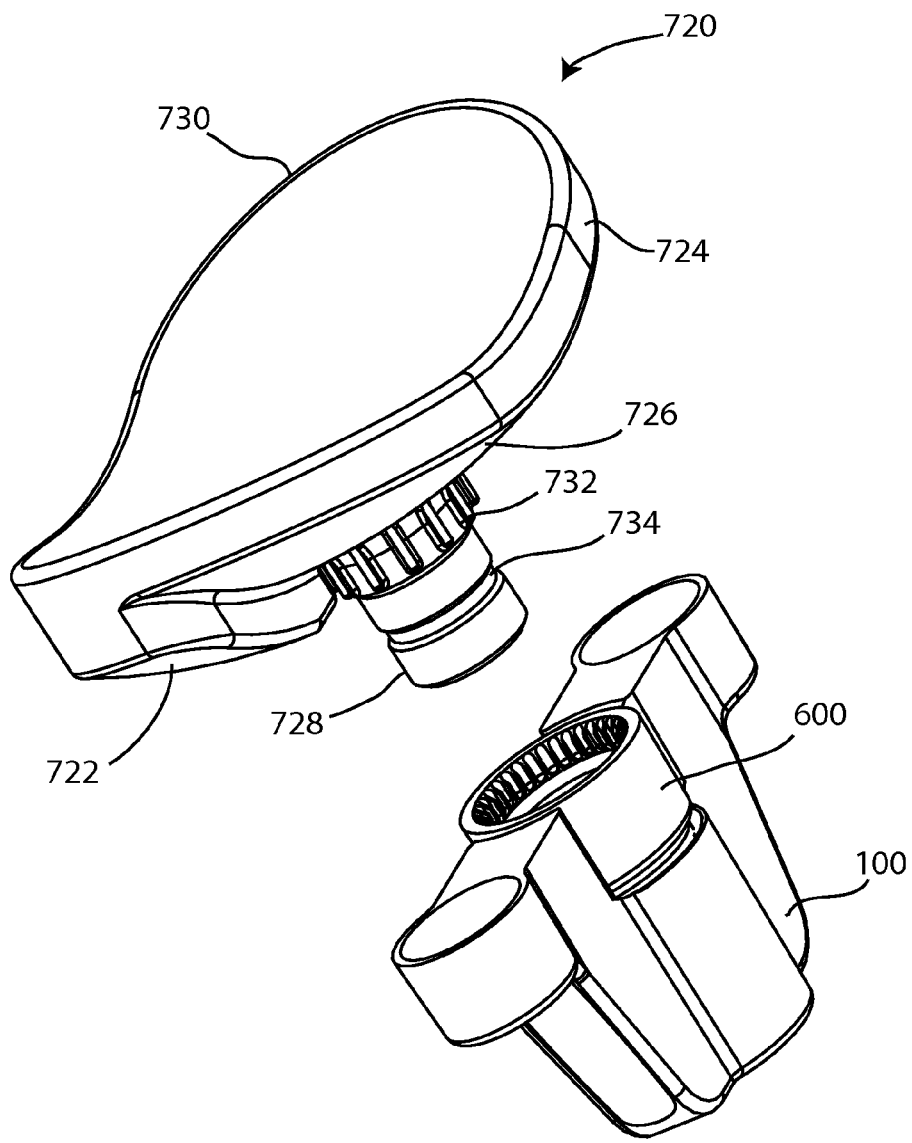
FIG. 20 is a partially exploded perspective view of the SI component of FIG. 1 or 15, the cylindrical component of FIG. 18 and an articulating component with augment.
Figure 21:
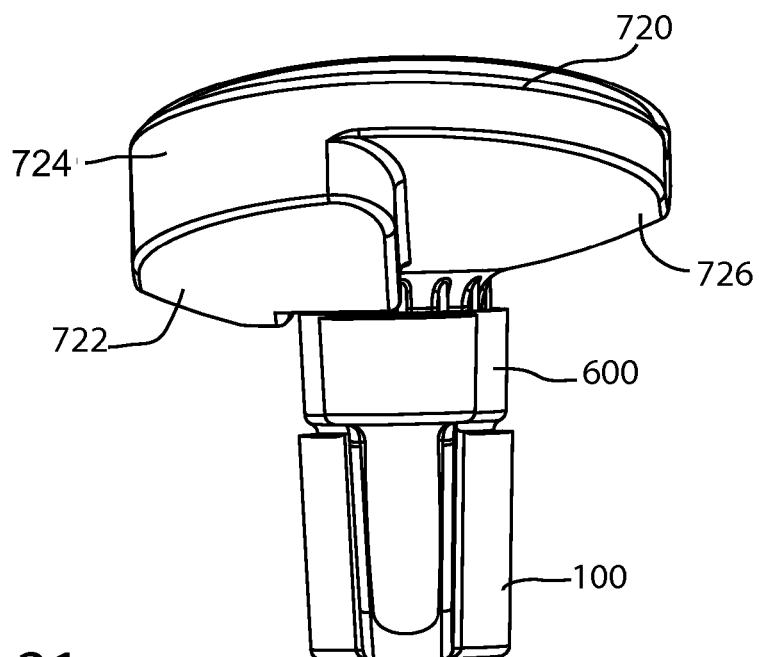
FIG. 21 is an assembled side view the SI component of FIG. 1 or 15, the cylindrical component of FIG. 18 and the articulating component with augment of FIG. 20.
Figure 22:
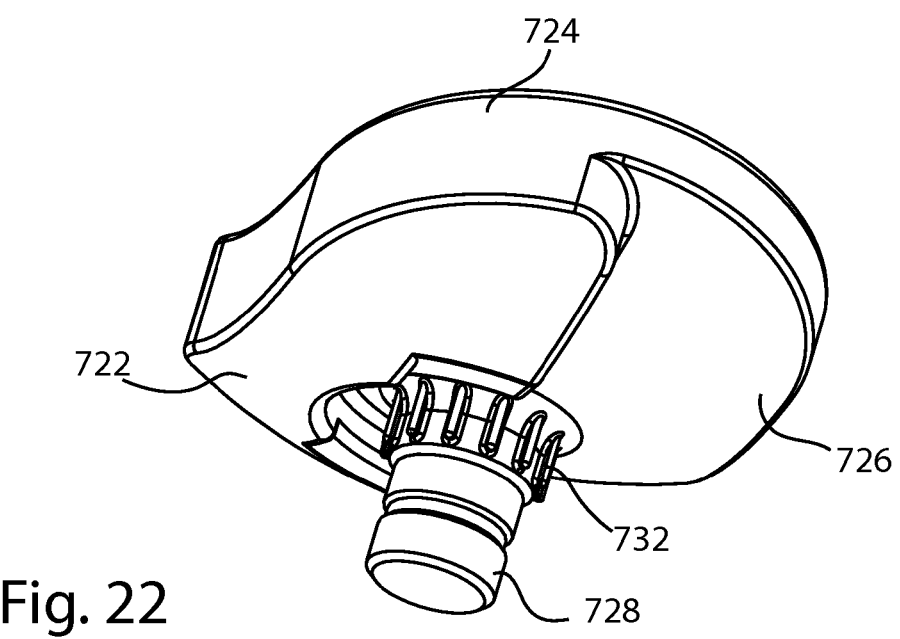
FIG. 22 is a bottom perspective view of the articulating component with augment of FIG. 20.

The cylindrical component 600 may be advantageously suited for use with an augmented articulating component or augmented glenosphere in that no arms, like those found in the other AP components 200, 500, are in the way of the augments on the articulating component and glenosphere designs. Referring to FIGS. 20-22, an articulating component 720 includes an augment 722 as part of the articulating component, essentially a one-piece articulating component with augment. A peripheral wall 724 extends from an articulating surface 730 to the bone-facing surface 726. The augment 722 may be separate from a post 728 and extend from a bone facing side 726 separate from where the post 728 extends from the bone facing side 726. The articulating component 720 further includes notches 732 that interact or engage the grooves or notches 612 of the cylindrical component in much the same manner as the previous embodiment forming a complimentary fit preventing rotation of the articulating component 720. The post 728 may further include the ring shaped cutout 734 for locking the articulating component 720 to the cylindrical component 600.

The augment 722 may also be rounded or smoothly tapered extending from the peripheral wall 724. The augment 722 may extend from the peripheral wall 724 toward a medial line or middle point of the articulating component 720 and wrap around the post 728 but not contacting the post 728. The post 728 may be greater in length than the augment 722. The augment 722 of the articulating component 720 is to replace that area of the shoulder where bone may be removed, as is the case with all the augment designs disclosed herein.

Figure 23:
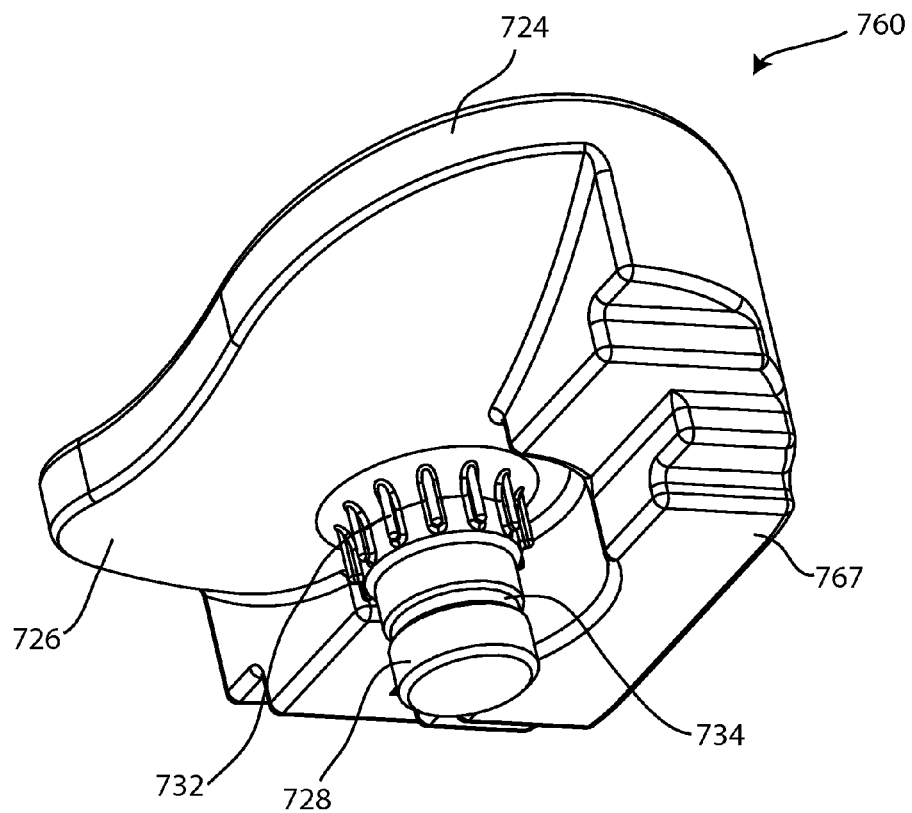
FIG. 23 is a bottom perspective view of an articulating component with stepped augment.

Referring to FIG. 23, an alternate embodiment of an articulating component 760 may include an augment 767 with a step-down taper. The step-downs may step down both peripherally and in a lateral direction from a middle point or medial line of the articulating component 760. The remainder of the alternate embodiment may be substantially similar as the previous articulating component 720 embodiment.

Figure 24:
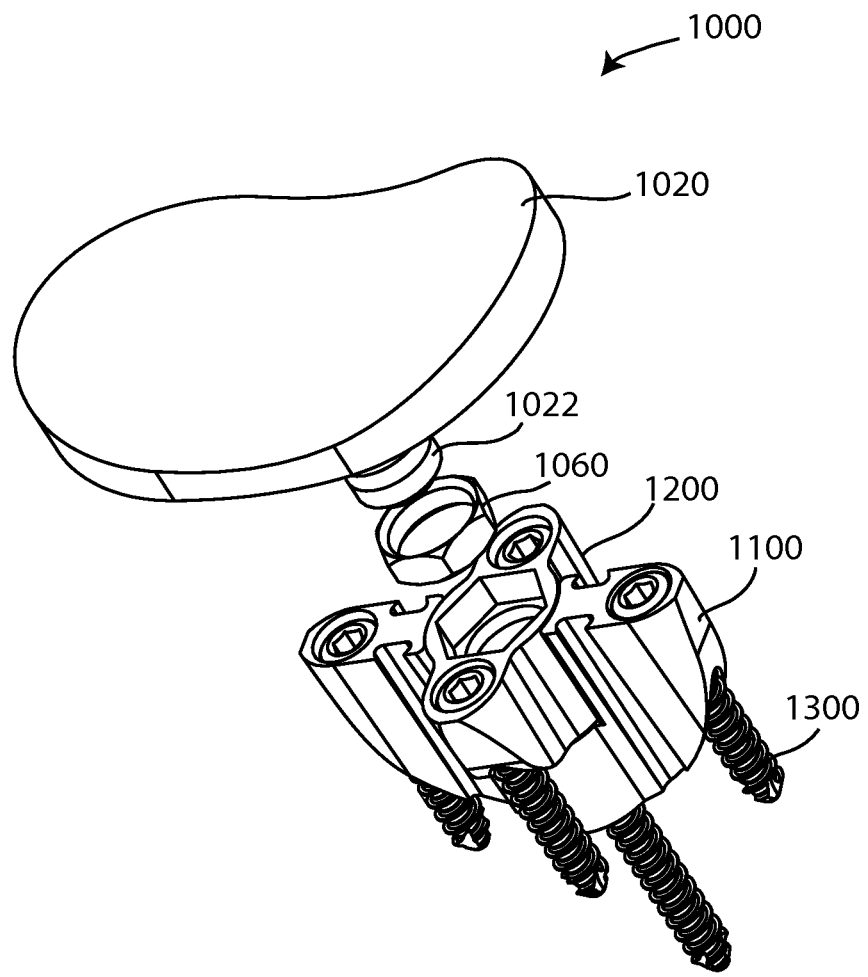
FIG. 24 is a partially exploded alternate embodiment of a glenoid vault system with a horizontal member, vertical member, screws, a hex component and an articulating component.
Figure 25:
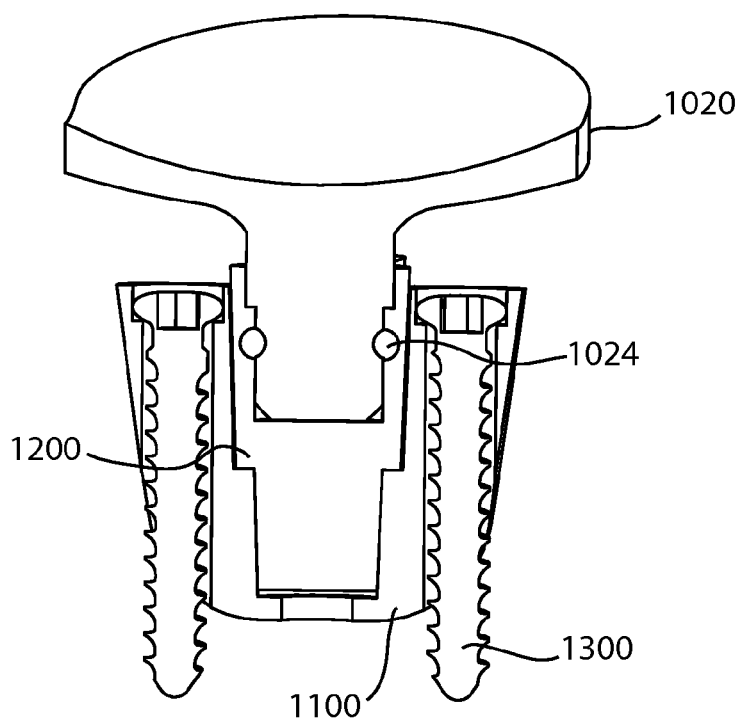
FIG. 25 is a cross sectional side view of the glenoid vault system of FIG. 24 with the horizontal member extending across the page.

Referring to FIGS. 24 and 25, there is depicted an alternate embodiment of a glenoid vault system 1000. The components in this embodiment are similar to the previous system 10. An articulating component 1020 is substantially similar to the previous embodiment articulating component 20; however the articulating component 1020 does not include notches to prevent rotation of the articulating component 1020. In this embodiment a polygon, or keyed, component 1060 that includes a cylindrical hole 1062, is inserted onto or wraps around a post 1022, which may be cylindrical in shape, of the articulating component 1020. The polygon component 1060 may be press fit onto the post. The polygon component 1060 may be hexagonal in shape. The polygon component 1060 engages a complimentary recess within an AP component 1200, preventing rotation of the articulating component 1020.

The post 1022 includes substantially the same feature of a cutout configured to interact with an engagement ring on the AP component 1200 to lock the post 1022 to the AP component 1200. The lock may be a snap fit, or seal 1024, or other locking means including a Morse taper (not shown) which may not require an engagement ring.

Figure 26:
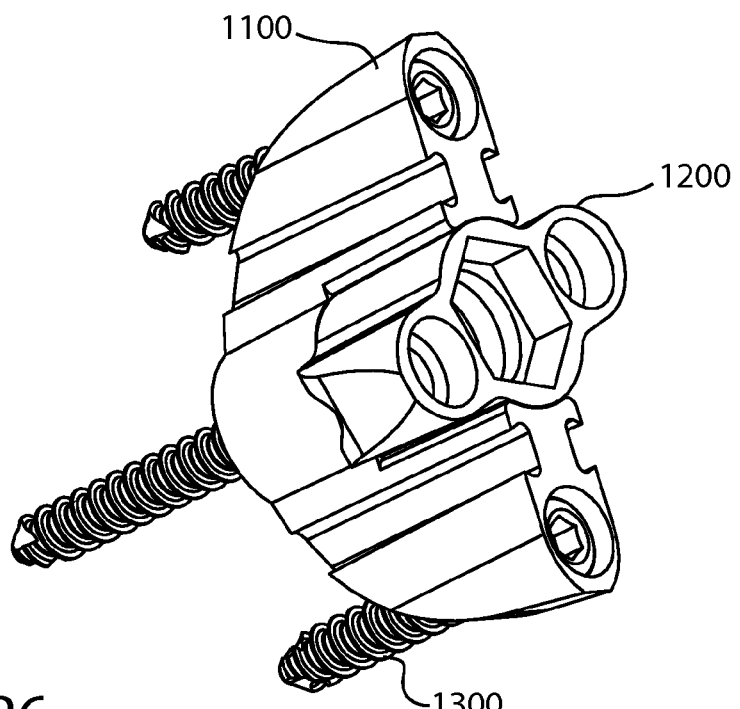
FIG. 26 is a perspective view of the vertical and horizontal members of FIG. 24.
Figure 27:
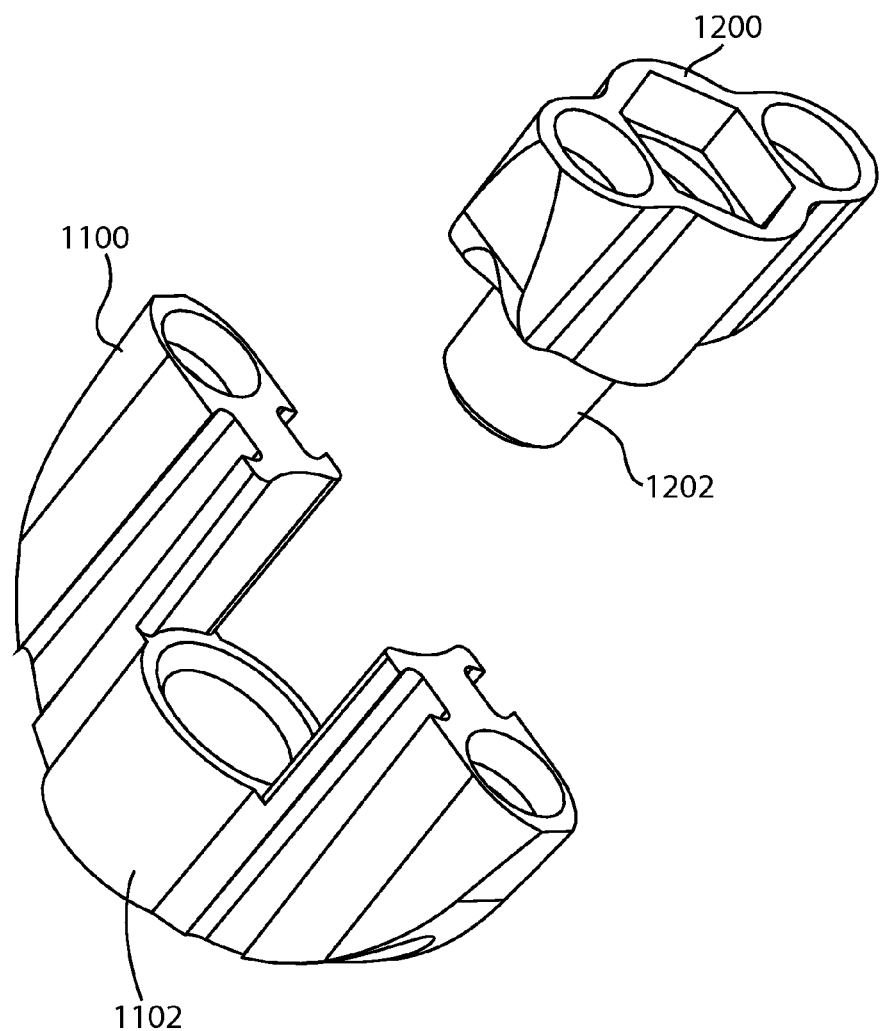
FIG. 27 is an exploded perspective view of the vertical and horizontal components of FIG. 24.

Referring to FIGS. 26 and 27, the glenoid vault system 1000 also includes an SI component 1100 and AP component 1200 and anchors or screws 1300 similar to the previous system 10. The features of these components differ slightly and will be described further herein. The interaction between the SI component 1100 and AP component 1200 is substantially the same as the previous system 10. A tubular boss 1202 of the AP component may slideably engage a central ring 1102 of the SI component, allowing the AP component to rotate within the central ring 1102. A9

Figure 28:
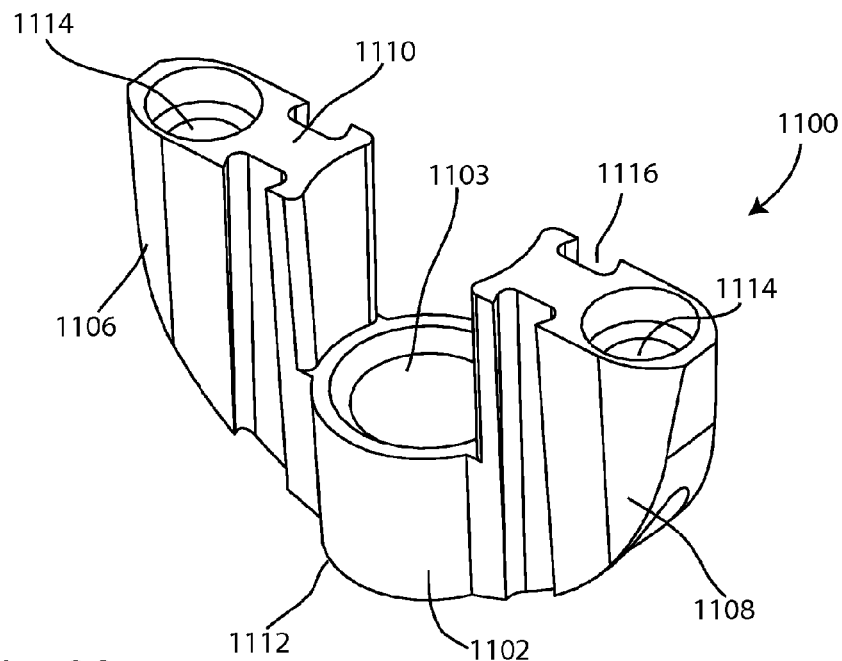
FIG. 28 is a perspective view of the vertical component of FIG. 24.
Figure 29:
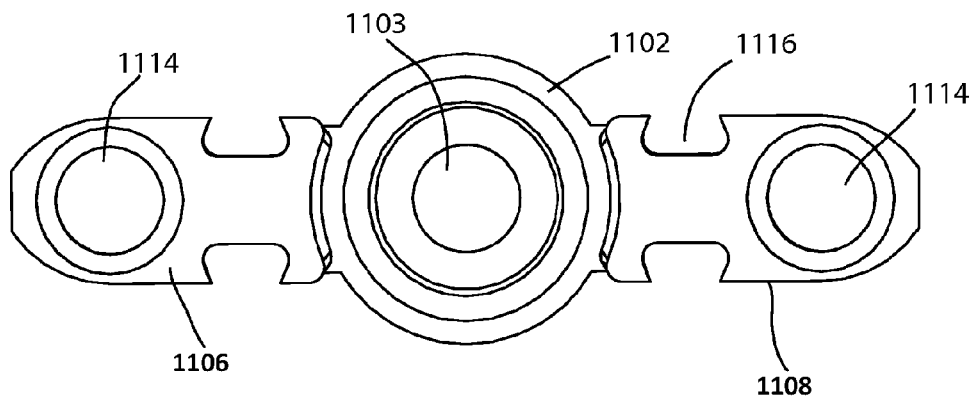
FIG. 29 is a top view of the vertical component of FIG. 24.

Referring to FIGS. 28 and 29, the SI component 1100 includes a central bore 1103 passing entirely through the central ring 1102 and arms 1106, 1108 extending from the central ring 1102. The arms 1106, 1108 extend in a wing-like manner from the central ring 1102 curvedly tapering from a proximal end 1110 toward a distal end 1112. Instead of rings extending from the arms as in the previous embodiment, the arms include openings 1114 that may extend entirely through the arm to receive screws 1300 (not shown) in substantially the same manner as previously described in the previous embodiment. The arms 1106, 1108 may include tracks 1116 for receiving an augment (as depicted in FIGS. 34-38). The tracks 1116 may be dovetail shaped and may be on either side of the arms 1106, 1108, on one arm or both arms. The tracks 1116 may run partially or entirely from the proximal end 1110 to the distal end 1112. The SI component 1100, from a profile view, may be U-shaped.

Figure 30:
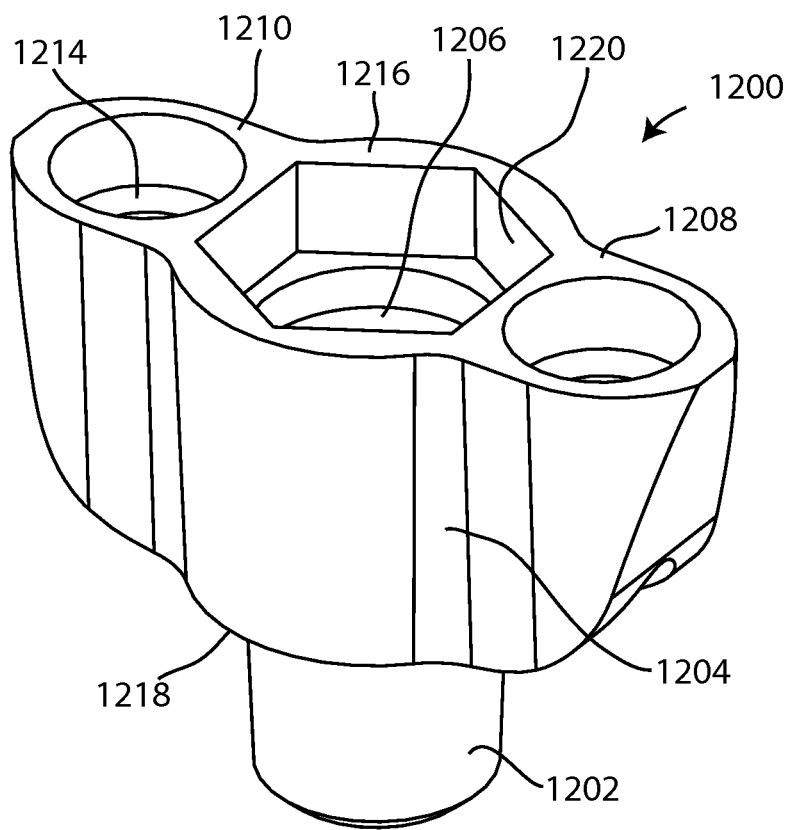
FIG. 30 is a perspective view of the horizontal component of FIG. 24.
Figure 31:
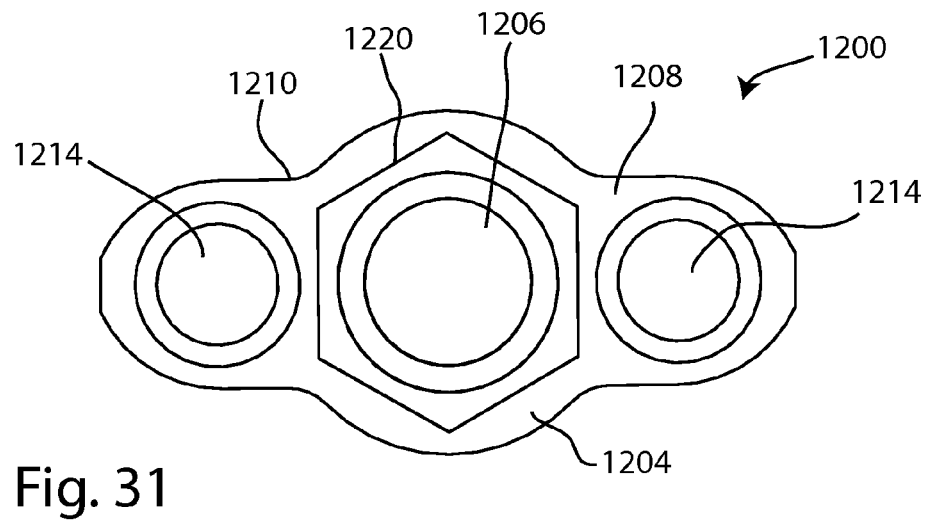
FIG. 31 is a top view of the horizontal component of FIG. 24.
Figure 32:
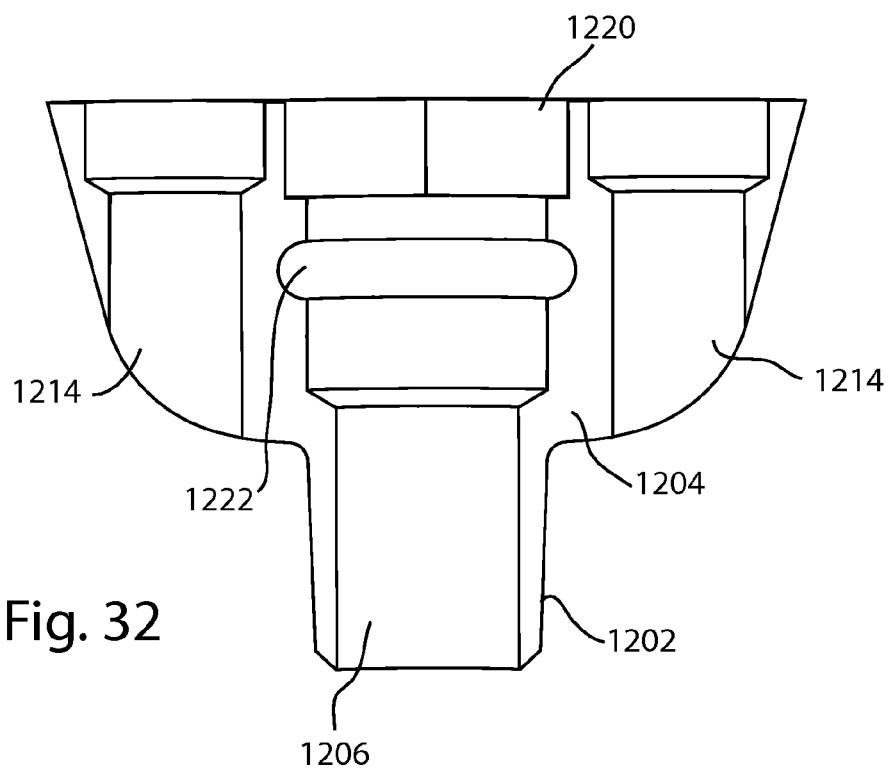
FIG. 32 is a cross sectional side view of the horizontal component of FIG. 24.

Referring to FIGS. 30-32, the AP component 1200 includes the tubular boss 1202 and a body 1204, with a central hole 1206 passing entirely through the center of the body 1204 and through the tubular boss 1202. The tubular boss 1202 may extend from the center of the body 1204 at a distal end 1218 of the AP component 1200. The AP component 1200 also includes AP arms 1208, 1210 extending similarly to the arms of the SI component 1100. The AP arms 1208, 12010 extend from the center of the body 1204 at the distal end 1218 toward a proximal end 1216 in a wing-like manner, curvedly tapering from the proximal end 1216 toward the distal end 1218. The arms include holes 1214 that may extend entirely through the arm to receive screws 1300 in substantially the same manner as the previously embodiment.

The AP component 1200 further includes a polygon recess or polygon key 1220 toward the proximal end 1216 within the body 1204 of the AP component 1200. The polygon recess 1220 provides complimentary fit for the polygon component 1060 wherein the polygon component 1060 may, but is not required to, sit flush with the proximal end 1216 within the polygon recess 1220. Within the central hole 1206 is an engagement ring 1222 that is substantially similar to the previous embodiment and interacts in substantially the same way to form a snap fit or seal or other similar locking mechanism including a Morse taper (not shown) which may not require an engagement ring.

Figure 33:
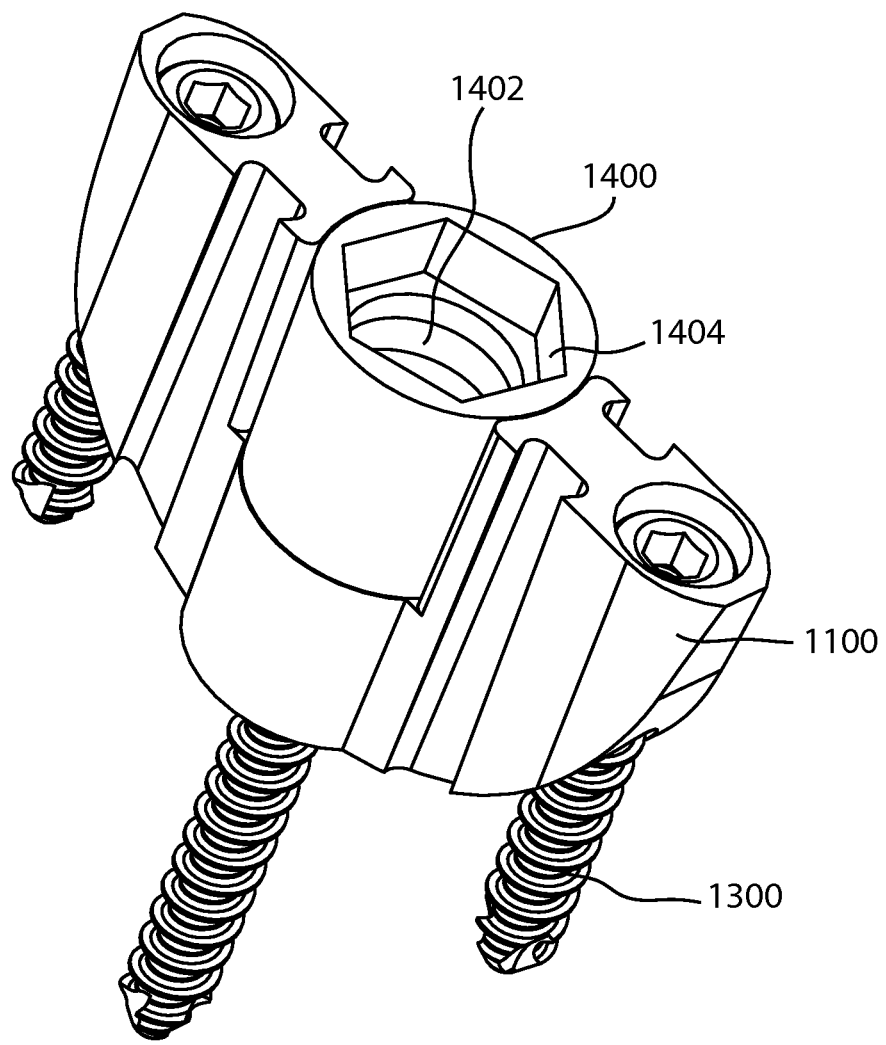
FIG. 33 is a perspective view of the vertical component of FIG. 24 and a cylindrical member.

Referring to FIG. 33, an alternate embodiment a cylindrical component 1400 with features of the AP component 1200 is shown, and is similar to the cylindrical component 600. The elements of the body of the AP component 1400 are substantially similar to component 600, having a tubular boss (not shown but within the central bore of the SI component 1100), a central hole 1402 and a polygon recess 1404. The cylindrical component may also include an engagement ring as previously described to lock the articulating component 1020 to the AP component 1400. This embodiment lacks arms and may be better suited to receive augments like those depicted in FIGS. 34-38.

Figure 34:
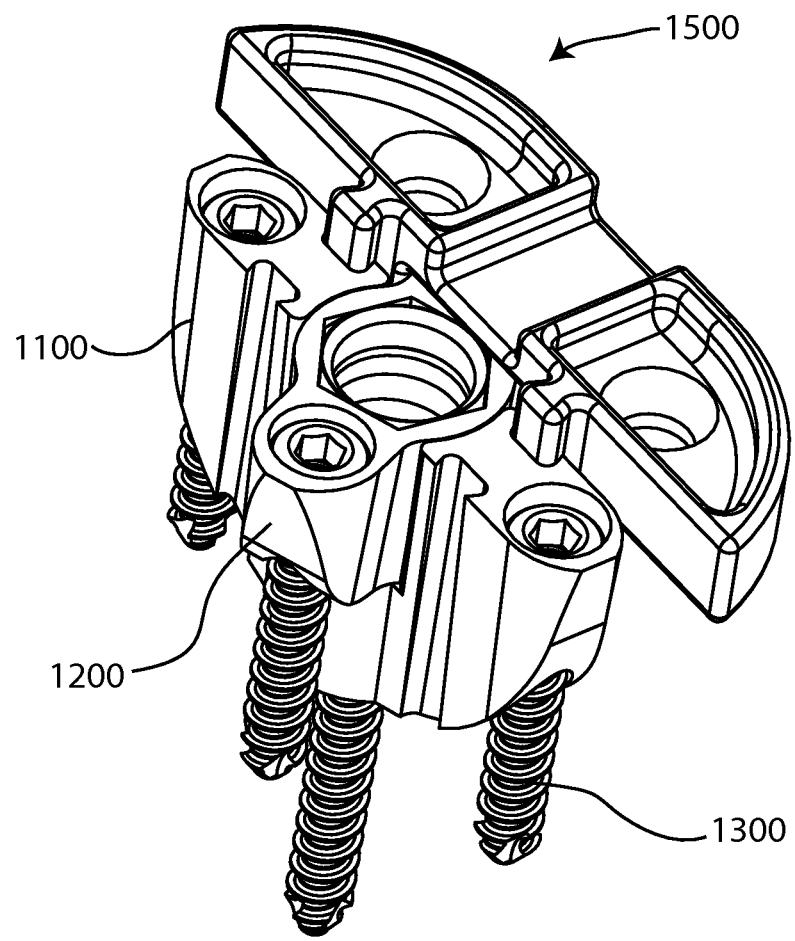
FIG. 34 is a perspective view of the vertical and horizontal component of FIG. 25 with an augment member.
Figure 35:
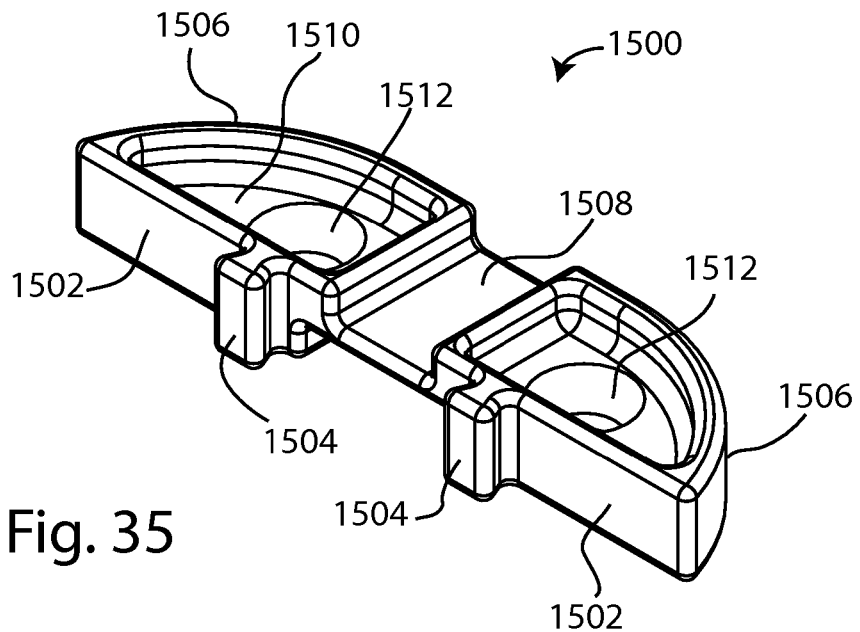
FIG. 35 is a perspective view of the augment member of FIG. 34.
Figure 36:
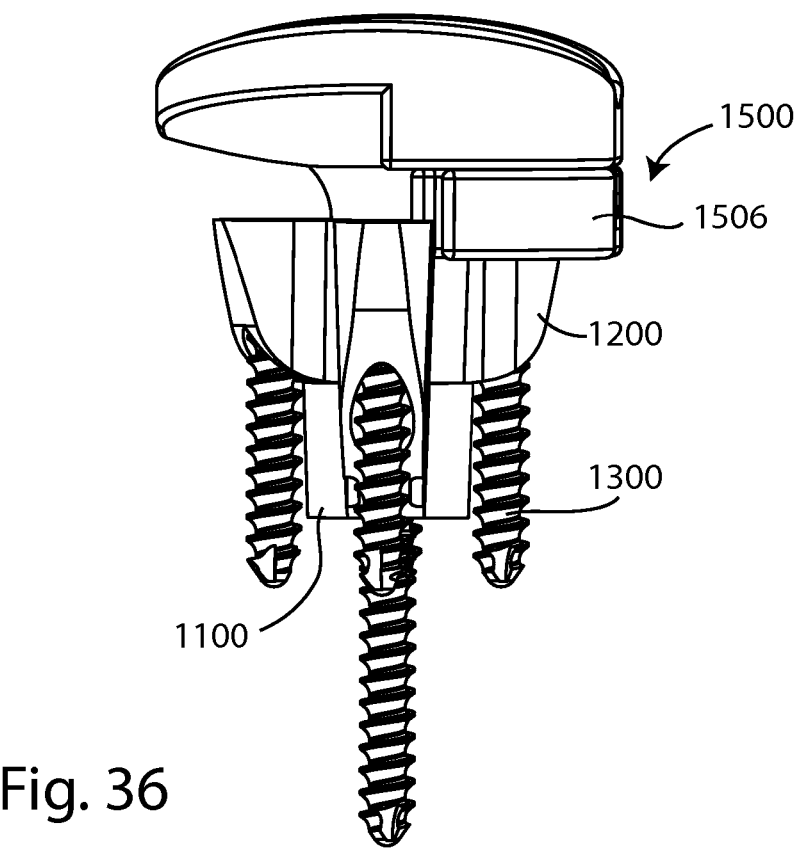
FIG. 36 is a side view of the glenoid vault system of FIG. 24 with the augment of FIG. 35.

Referring to FIGS. 34-36, an augment 1500 is shown with the SI component 1100 and the AP component 1200. The augment 1500 includes a straight edge 1502 with two dovetailed protrusions 1504 spaced apart from one another, perpendicular to the straight edge 1502, and configured to slide in the tracks 1116 of the SI component 1100. The straight edge 1502 terminates on each end of the augment where two curved edges 1506 arch back toward a midline of the augment 1500. A valley 1508 may divide the augment into two mirror image sides wherein each side of the augment includes a pocket 1510 which may receive a partial augment from the articulating component 1020 similar to the partial augment of articulating component 420 or the one-piece augment articulating components 720, 760. The pockets 1510 may include holes 1512 passing through the augment 1500 to allow for passage of screws 1300 to secure the augment 1500 to the bone.

Figure 37:
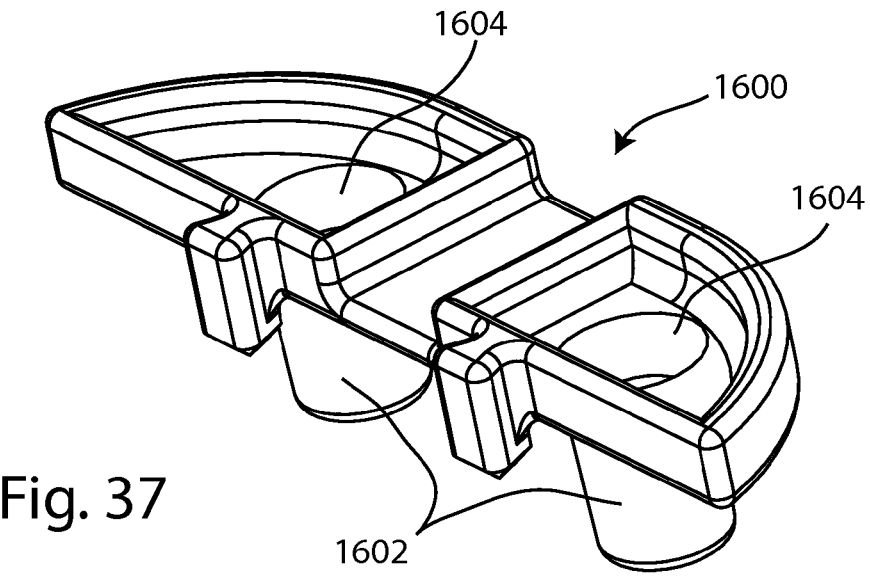
FIG. 37 is a perspective view of an alternate augment.
Figure 38:
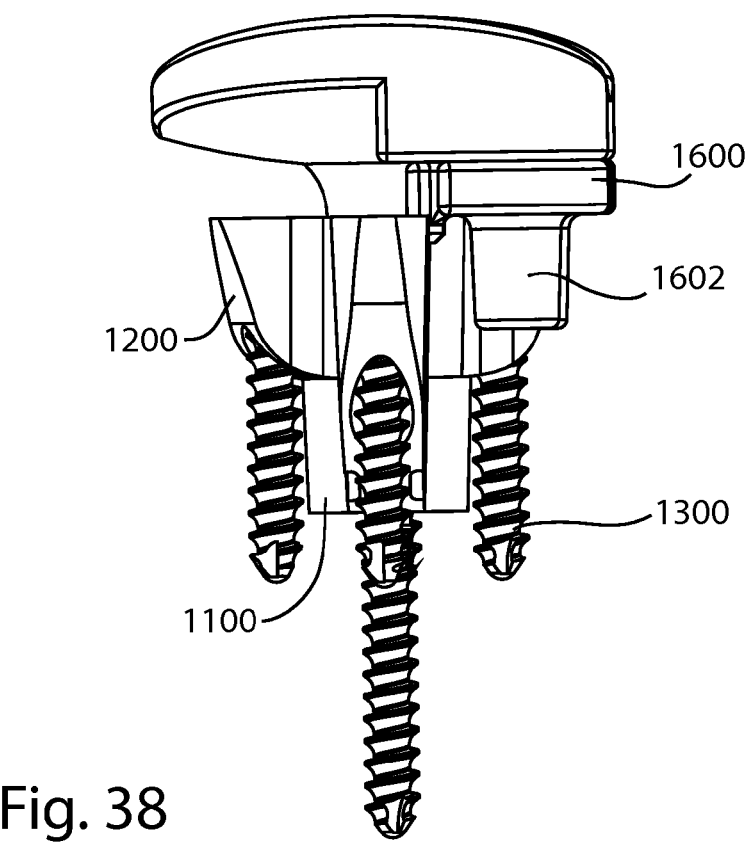
FIG. 38 is a side view of the glenoid vault system of FIG. 24 with the augment of FIG. 37.

Referring to FIGS. 37 and 38, an augment 1600 may include substantially the same features of the augment 1500; however, the augment 1600 may include tubular bosses 1602 extending in a direction away from the articulating component essentially extending the length of holes 1604 for receiving the screws 1300. The screws 1300 may secure the augment 1600 to the bone.

Figure 39:
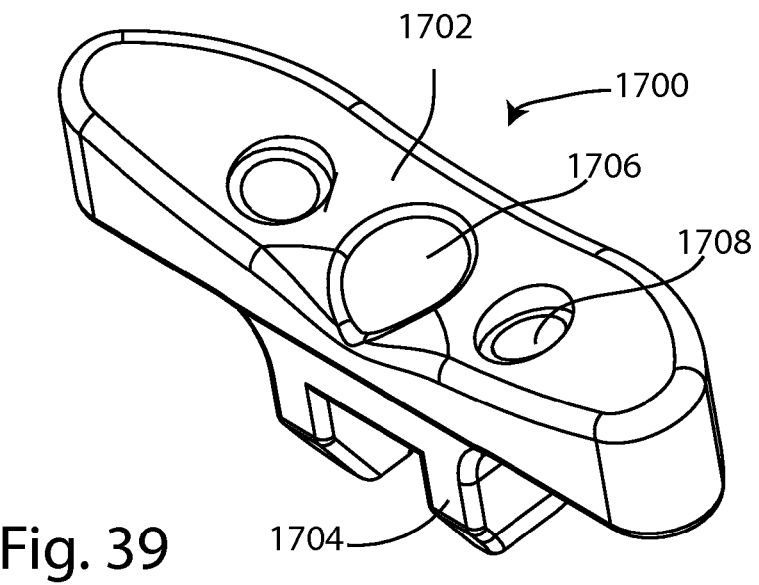
FIG. 39 is a perspective view of an alternate augment.
Figure 40:
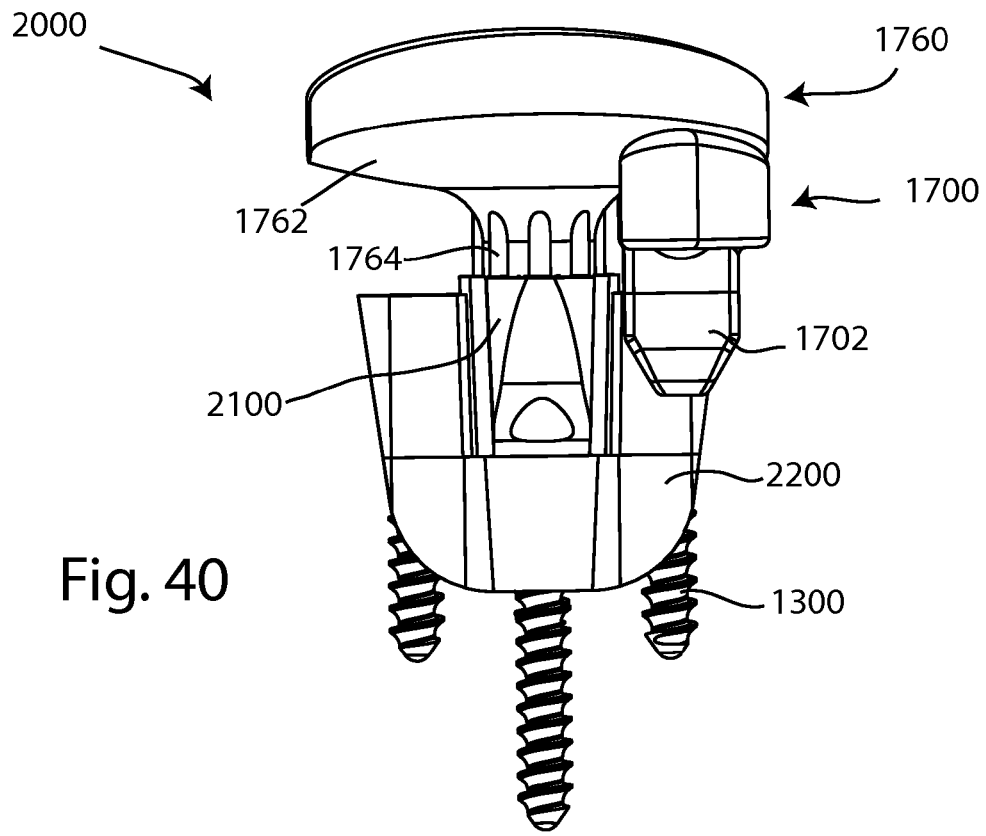
FIG. 40 is a side view of the glenoid vault system of FIG. 24 with the augment of FIG. 39.
Figure 41:
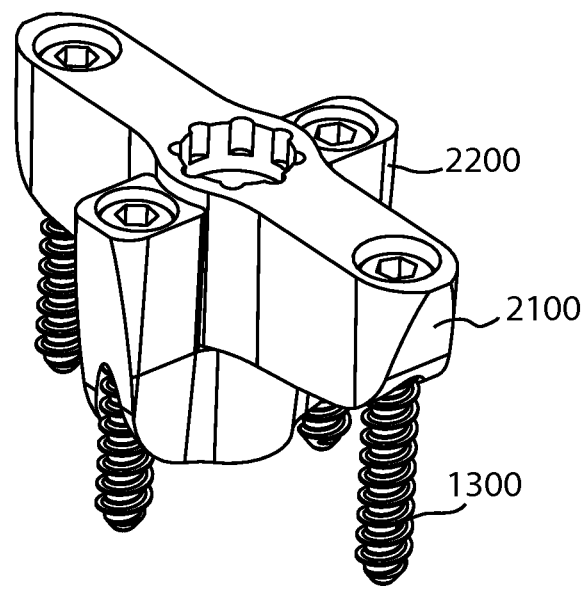
FIG. 41 is a perspective view of an alternate embodiment of an anchoring system for the glenoid vault with an alternate vertical member and horizontal member and screws.
Figure 42:
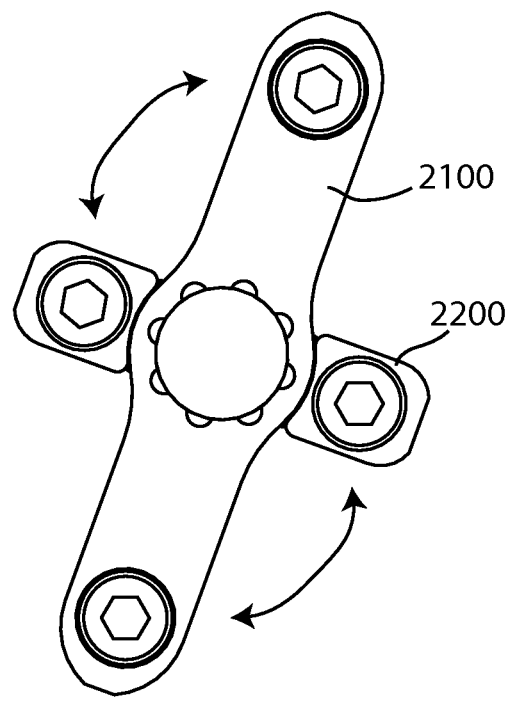
FIG. 42 is a top view of the alternate embodiment anchoring system of FIG. 41 with the vertical component rotated to show it is rotatable about the center of the horizontal component.
Figure 43:
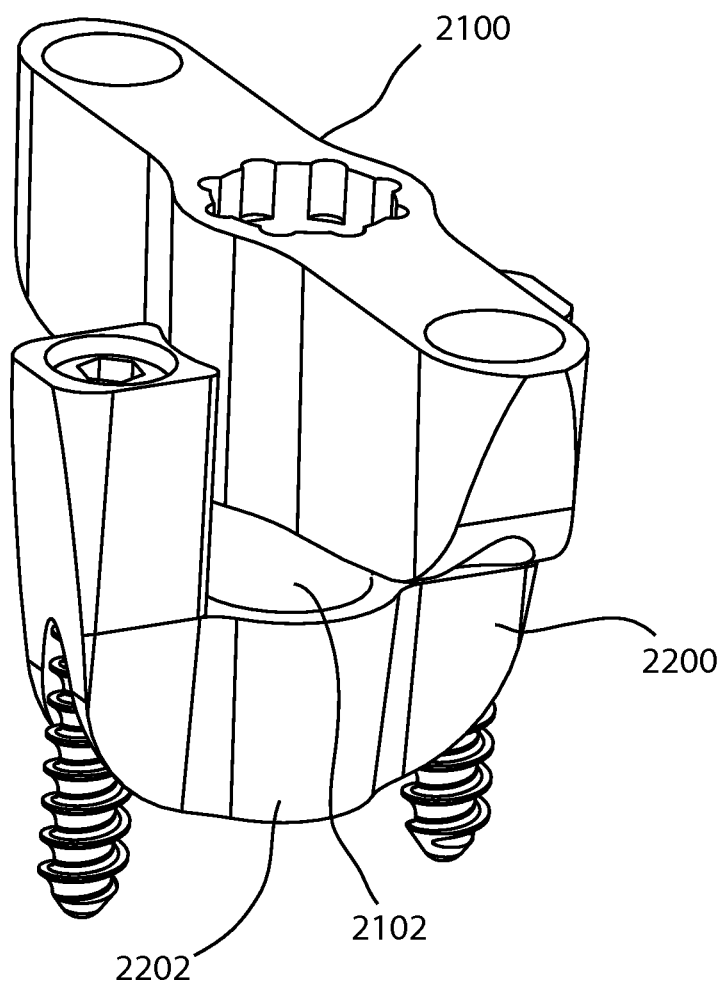
FIG. 43 is a perspective view of the anchoring system of FIG. 41 with the vertical member slightly exploded from the horizontal member.

Referring to FIGS. 39 and 40, an augment 1700 includes a curved surface 1702 shaped to lie against a bone facing surface 1762 of an articulating component 1760. The curvature of the curved surface 1702 may match the curvature of the bone facing surface 1762. Extending from the opposite side of the curved surface 1702 of the augment 1700 is a saddle 1704 that straddles a horizontal or AP component 2200. The augment 1700 may include a centralized hole 1706 passing through the body of the augment 1700 as well as additional holes 1708 passing through the body of the augment 1700 to allow for passage of screws to secure the augment 1700 to the bone.

Referring to FIGS. 40-43, an alternate embodiment of a glenoid vault system 2000 is depicted with a vertical or SI member 2100, a horizontal or AP member 2200, screws 2300 and an articulating component 1750. The augment 1700 may or may not be present in this embodiment. This system 2000 is similar to the previously disclosed systems 10, 1000 with the exception that a portion of the vertical member 2100 fits in the horizontal member 2200 instead of vice versa. In this instance the horizontal member 2200 is embedded into the bone and then a portion of the vertical member 2100 slides into a portion of the horizontal member 2200.

The horizontal member 2200 includes all of the same elements as previously described for a previously described AP component 200 with the exception that the features of the central rings 102, 1102 of the previous embodiments are now found in the horizontal member 2200 instead of the vertical member 2100. The horizontal member 2200 is embedded in the bone in an anterior posterior direction first and then the vertical member 2100 is embedded in the bone in a generally superior inferior direction. The horizontal member 2200 includes a central ring 2202 that is large enough to receive a tubular boss 2102 extending from the vertical member 2100.

Figure 44:
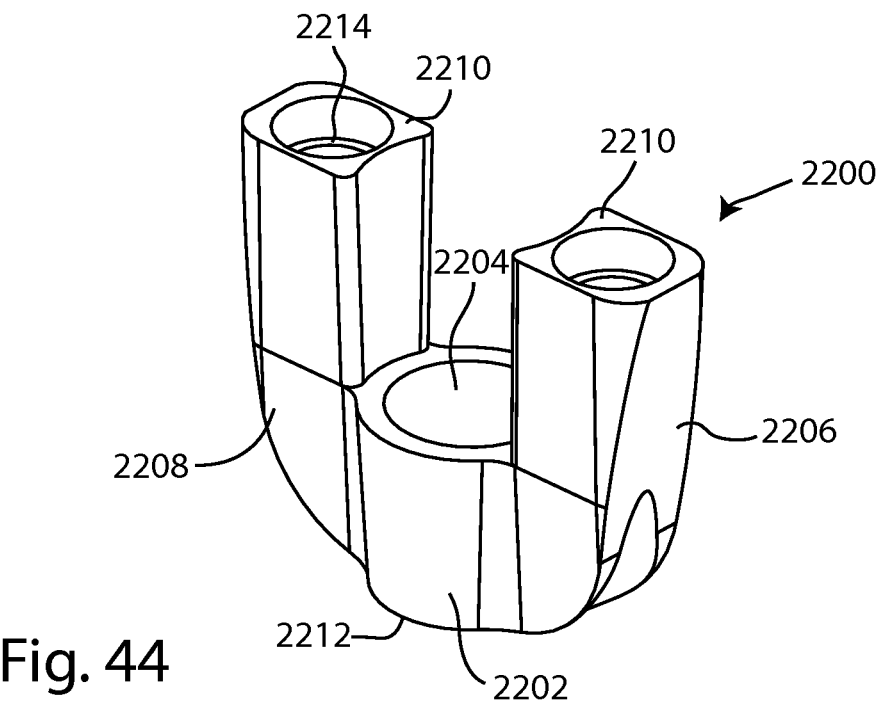
FIG. 44 is a perspective view of the horizontal member of FIG. 41.

Referring to FIG. 44, the horizontal member 2200 includes the central ring 2202 that defines a central bore 2204 that may pass partially or entirely through the central ring 2202. A screw 1300 may pass through the central bore 2204 to aid in securing the horizontal member 2200 to bone. Arms 2206, 2208 extend from the central ring 2202 rather abruptly in a proximal direction terminating at a proximal end 2210. The arms 2206, 2208 may be somewhat longer from the proximal end to a distal end 2212 than previous embodiments of the SI components 100, 1100. The arms 2206, 2208 may each include a bore 2214 which extend the entire length of the arm from the proximal end 2210 to the distal end 2212 and are configured to receive screws 1300. The bores 2214 may surround a larger portion of the screws 1300 because of the greater length of the arms 2206, 2208 in a proximal/distal direction. Toward the distal end 2212 of the arms 2206, 2208 a portion of the arms 2208, 2008 on the lateral side may be cut away to expose the threads of the screw 1300 to allow for greater security and fixation of the screws 1300 to the bone. Many features of the horizontal member 2200 are similar to those of the previously disclosed SI components 100, 1100 including the curvature of the arms toward the central ring 2204 matching the curvature of the central ring 2204 to allow the vertical member 2100 to rotate.

Figure 45:
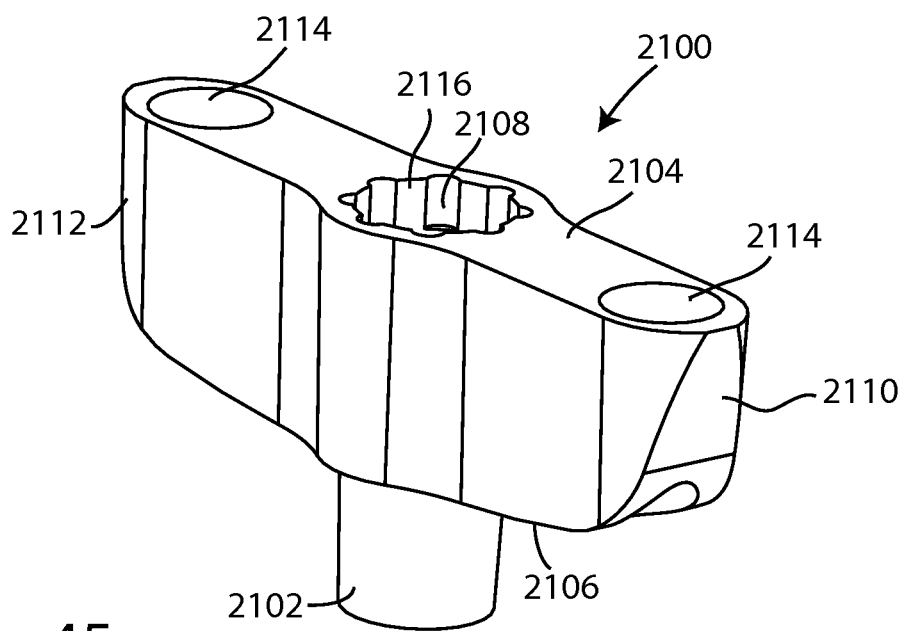
FIG. 45 is a perspective view of the vertical member of FIG. 41.

Referring to FIG. 45, the vertical member 2100 is short, narrow and elongated. The vertical member 2100 is stout from a proximal end 2104 to a distal end 2106. The tubular boss 2102 extends from the distal end and includes a portion of a central hole 2108 that may extend entirely from the proximal end 2104 to the distal end 2106 and through the entire length of the tubular boss 2102. The vertical member 2100 is elongated because of vertical member arms 2110, 2112 extending outwardly in opposite directions from the central hole 2108. The vertical member arms 2110, 2112 each include a hole 2114 to receive screws to secure the vertical member 2100 to the bone. The holes 2114 are separate from the central hole 2108. The walls within the central hole 2108 toward the proximal end 2104 may include grooves or notches 2116 that may form a keyed fit or complimentary interaction with articulating component notches 1764 seen in FIG. 40. These notches or grooves 2116 allow rotational orientation of the articulating component and prevent rotation of the articulating member 1760 after it engages the vertical member 2100. These notches or grooves 2166 may be rounded or squared or any shape that may prevent rotation and have the complimentary fit on the articulating component 1760.

The vertical member 2100 may also include an engagement ring (not shown) that is similar to the previous embodiment engagement ring 222. The engagement ring provides a reversible locking of the articulating component 1760 to the vertical member 2100 through a snap fit or seal, or other locking means including a Morse taper (not shown) which may not require an engagement ring, in substantially the same manner as previously disclosed.

The method for inserting the vertical and horizontal members into the bone is substantially similar as previously described except with the bone may require anterior-posterior preparation first instead of superior-inferior preparation. The order of implantation and interaction between the components can be changed and is not meant to be restrictive.

Referring to FIGS. 46-51, an alternate embodiment of a glenoid vault system 3000 with a horizontal member 3200 and vertical member 3100 is depicted. The system 3000 is substantially similar to the previous system 2000 with a few notable exceptions. Horizontal member tracks 3202 are in place of the bores 2214 in the arms 2206, 2208 of the horizontal member 2200. Likewise vertical member tracks 3102 are in place of the holes 2114 of the arms 2110, 2112 of the vertical member 2100. The tracks 3102, 3202 may be dovetailed to receive anchors 3300, which may be blade anchors similar to those found in U.S. published patent application no. 2010/0204739, which is herein incorporated by reference, and are further depicted in FIG. 50. Another type of anchor is that depicted in FIG. 51 and which provides an alternate embodiment of the anchor 3300. The anchor 3300 may be a bone-augmenting anchor 3302 that may provide for alternate fixation by adding greater size to the blade portion 3304. The blade portion 3304 of the bone-augmenting anchor may be rectangular or trapezoidal in cross sectional shape. The blade anchors 3300 may be embedded or inserted into the bone in the manner as described in the incorporated patent application.

The method for implantation using blade anchors 3300 may be slightly different simply because the blade anchors may require little to no bone preparation for securing those anchors to the bone and is outlined in the published patent application referenced herein.

Figure 46:
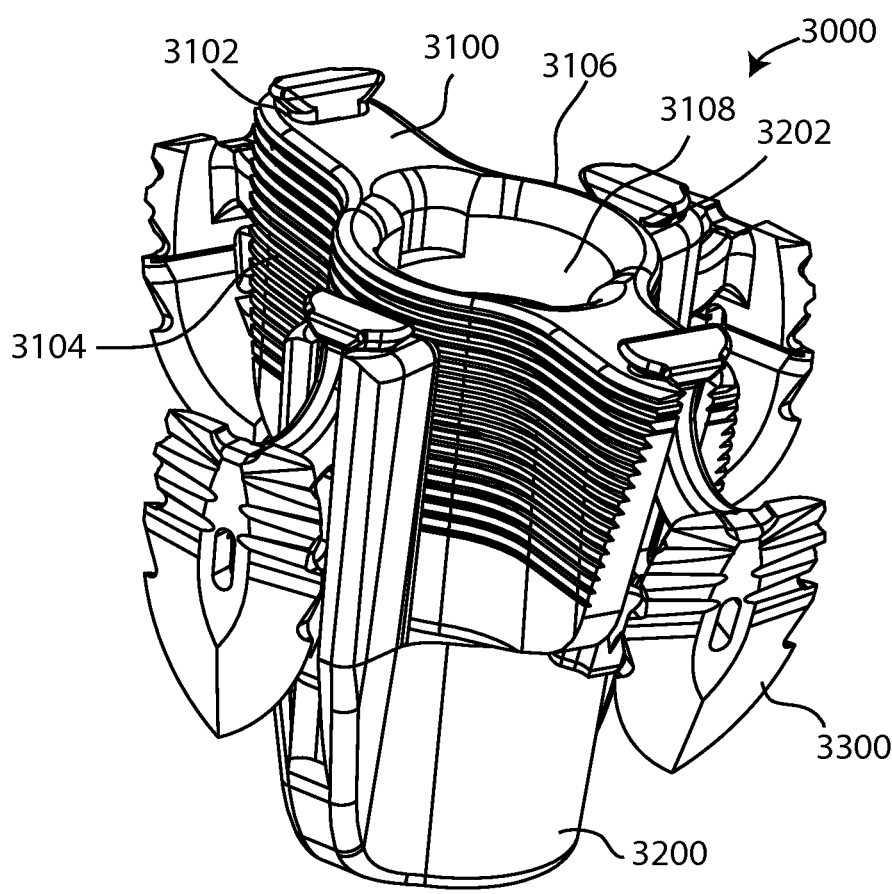
FIG. 46 is a perspective view of an alternate embodiment of an anchoring system for the glenoid vault with blade anchors.
Figure 47:
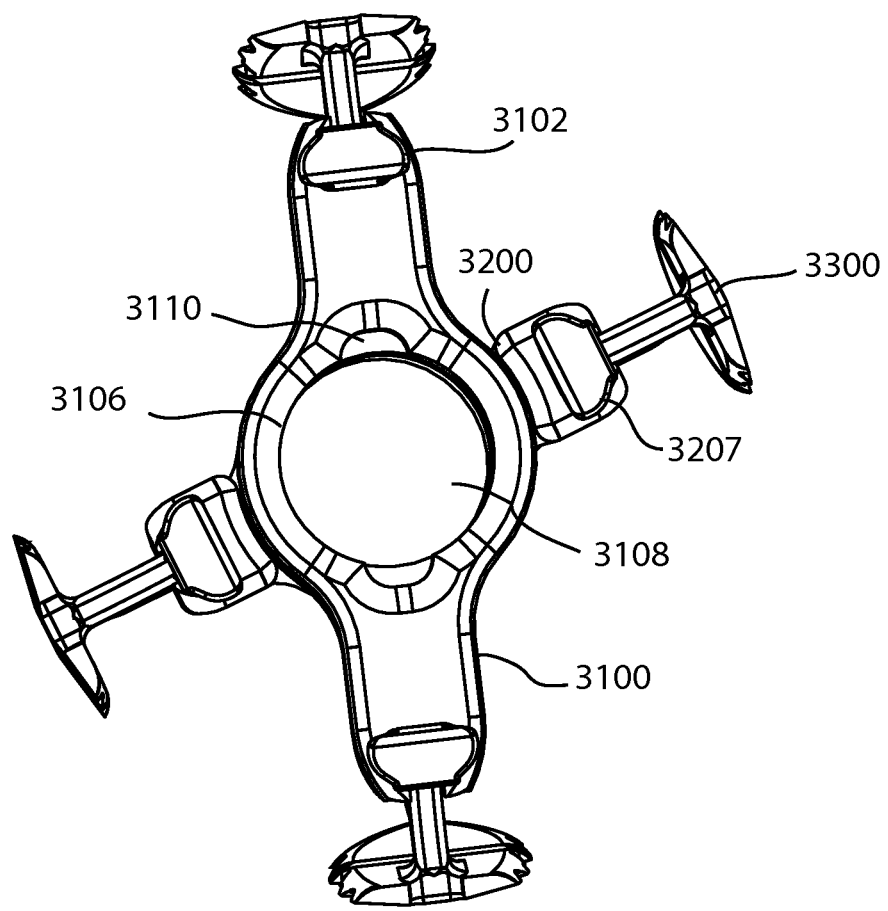
FIG. 47 is a top view of the anchoring system of FIG. 46.
Figure 48:
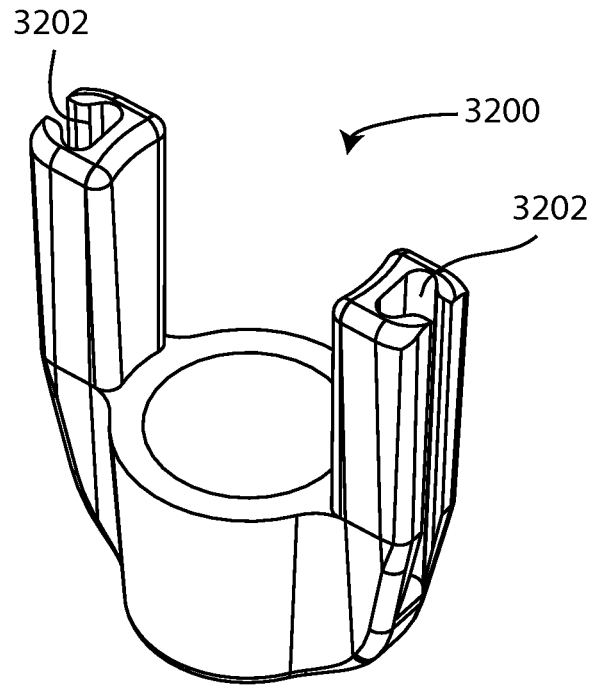
FIG. 48 is a perspective view of the horizontal member of FIG. 46.
Figure 49:
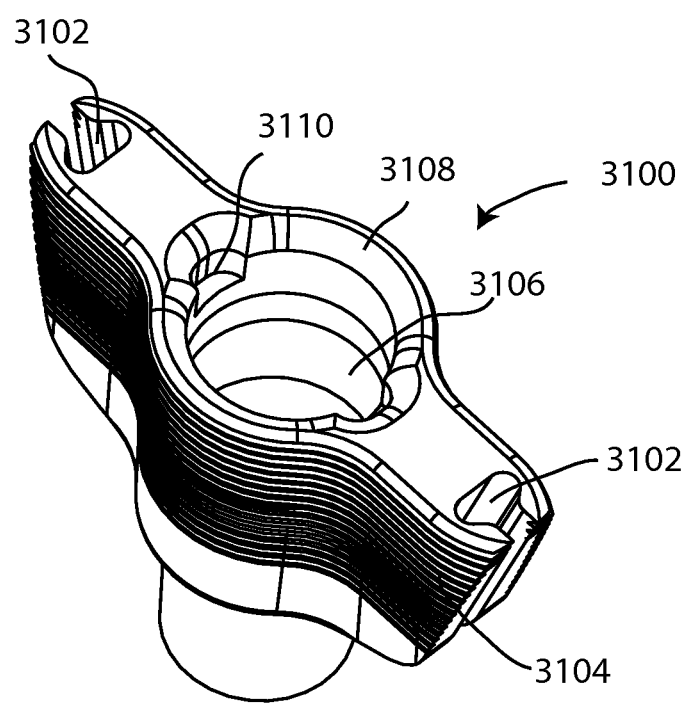
FIG. 49 is a perspective view of the vertical member of FIG. 46.
Figure 50:
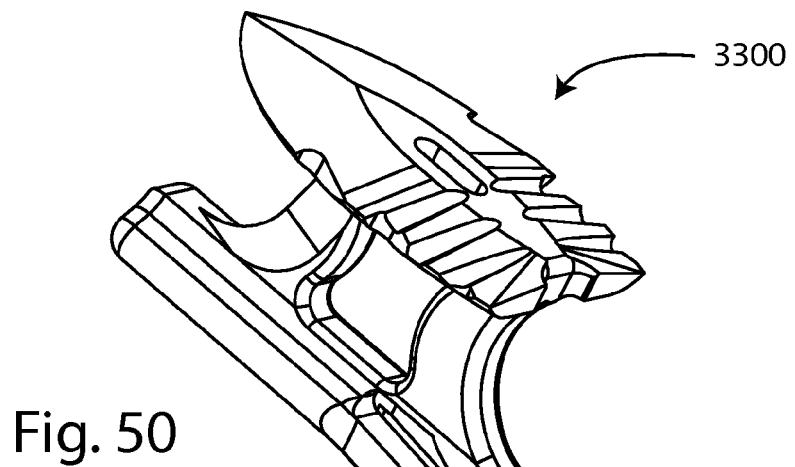
FIG. 50 is a perspective view of a sample blade anchor for use in the systems of FIGS. 46, 52 and 54.
Figure 51:
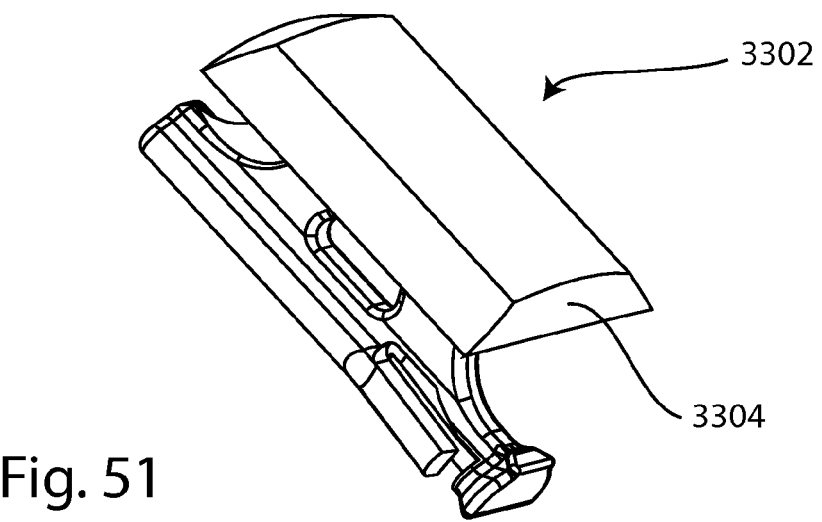
FIG. 51 is a perspective view of an alternate embodiment of an anchor with bone wall filler.

Referring to FIGS. 46 and 49, the vertical member 3100 also includes new Features such as roughened or interrupted surface geometry that may be circumferential ridges 3104 that may aid in preventing pull out of the vertical member 3000. Ridges 3104 may be used in all the previous embodiments as well. The vertical member 3100 also includes a wall 3106 cylindrically surrounding a central hole 3108. The wall 3106 includes at least two cutouts 3110 on opposing sides of the wall 3106 toward a proximal end. The cutouts 3110 provide a keyed or complimentary fit with an articulating component (not shown) to allow rotational orientation of the articulating component and prevent rotation of the articulating component after engaging the vertical member 3100. The shape, size and number of the cutouts may vary and may be similar to those previous described as notches or grooves herein.

Figure 52:
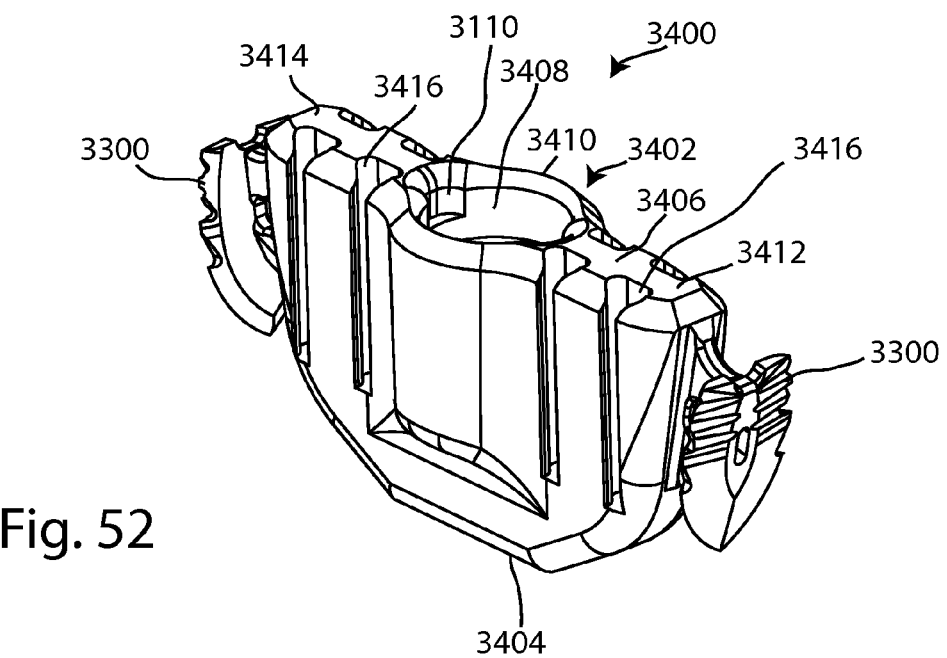
FIG. 52 is a perspective view of a one piece vertical member with built in anchors and slots to receive more anchors.
Figure 53:
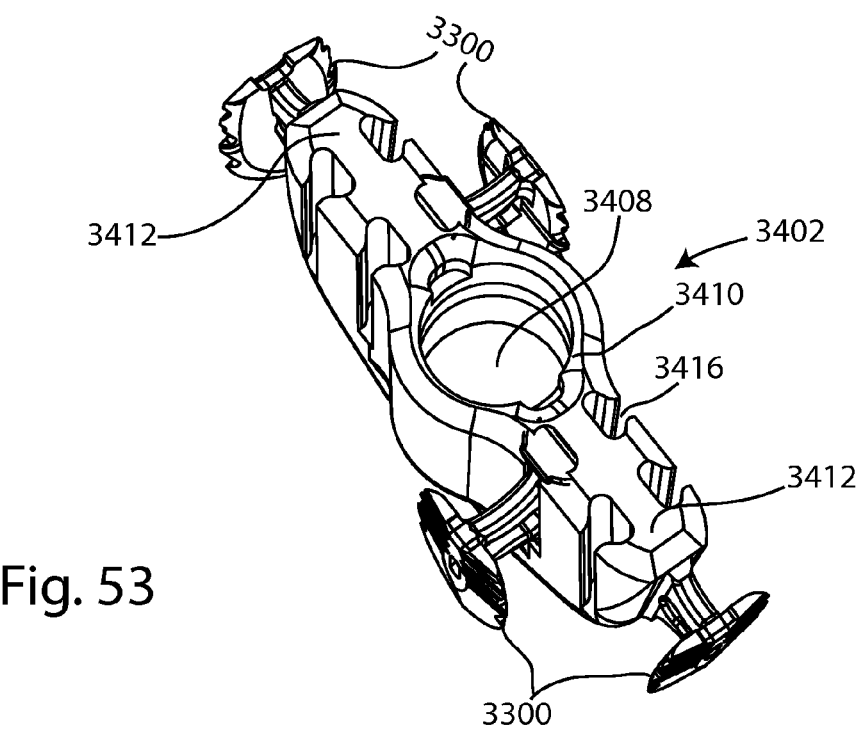
FIG. 53 is a top perspective view of the one piece vertical member of FIG. 50 with horizontal anchors in the slots.

Referring to FIGS. 52 and 53, a single anchoring system 3400 includes only a vertical member 3402 that is implantable in a shoulder in superior-inferior direction. The vertical member includes features substantially similar to the previous embodiment vertical member 3100; however the present embodiment does not interact with a horizontal member. This vertical member 3402 includes a distal end 3404, a proximal end 3406, and a central hole 3408 defined by a cylindrical wall 3410 substantially the same as the previous embodiment vertical member 3100 with the same cutouts 3110 as previously described. The central hole 3408 terminates just prior to a distal end 3404 and does not pass through the entire body of the vertical member 3402. Arms 3412, 3414 extend from the cylindrical wall 3406 in opposite directions away from the central hole 3408. The arms 3412, 3414 terminate with blade anchors 3300 integrally formed with the body of the vertical member 3400.

One or more tracks 3416 may be integrally formed within the body of the vertical member 3402 and extend from the proximal end 3406 toward the distal end 3404 terminating just prior to the distal end. The tracks 3416 may be dovetailed and are configured to receive anchors 3300. The number of tracks 3416 may vary and may extend from only one side of the arms 3412, 3414 or both sides. An articulating member may interact and engage the vertical member 3402 in much the same manner as any of the previous embodiment herein described.

Figure 54:
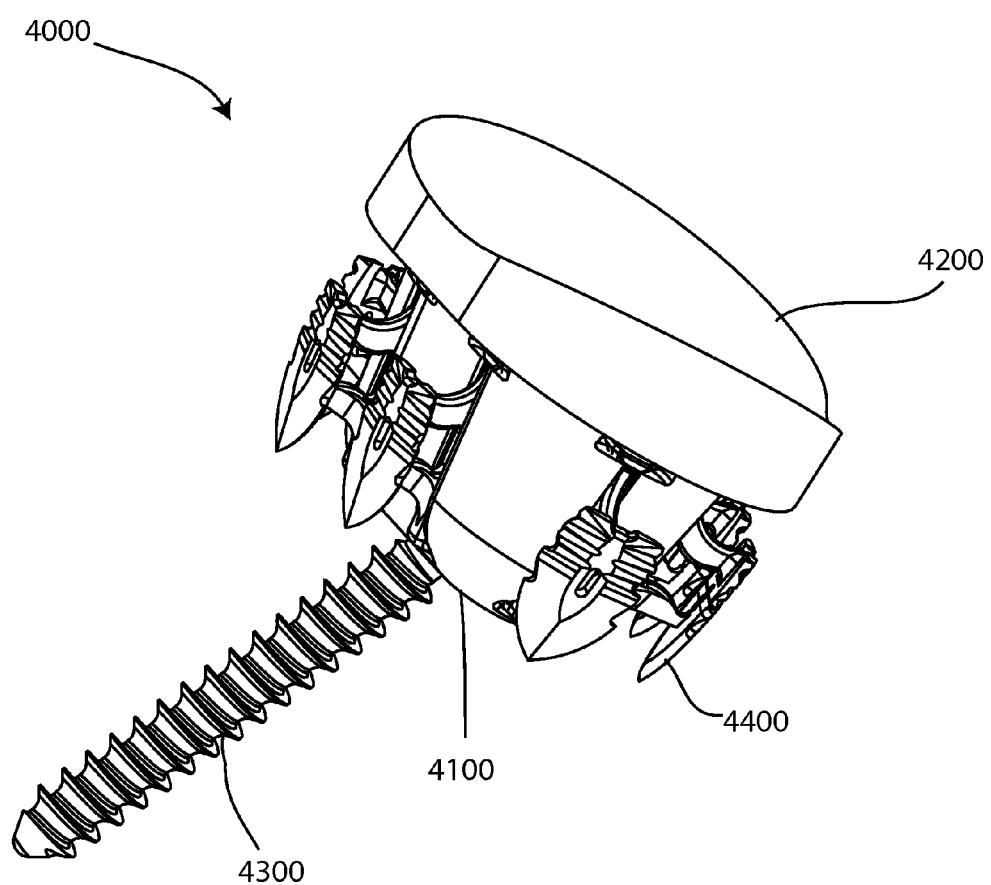
FIG. 54 is a perspective view of an alternate embodiment glenoid vault system with a vault, screw, anchors and glenoid.
Figure 55:
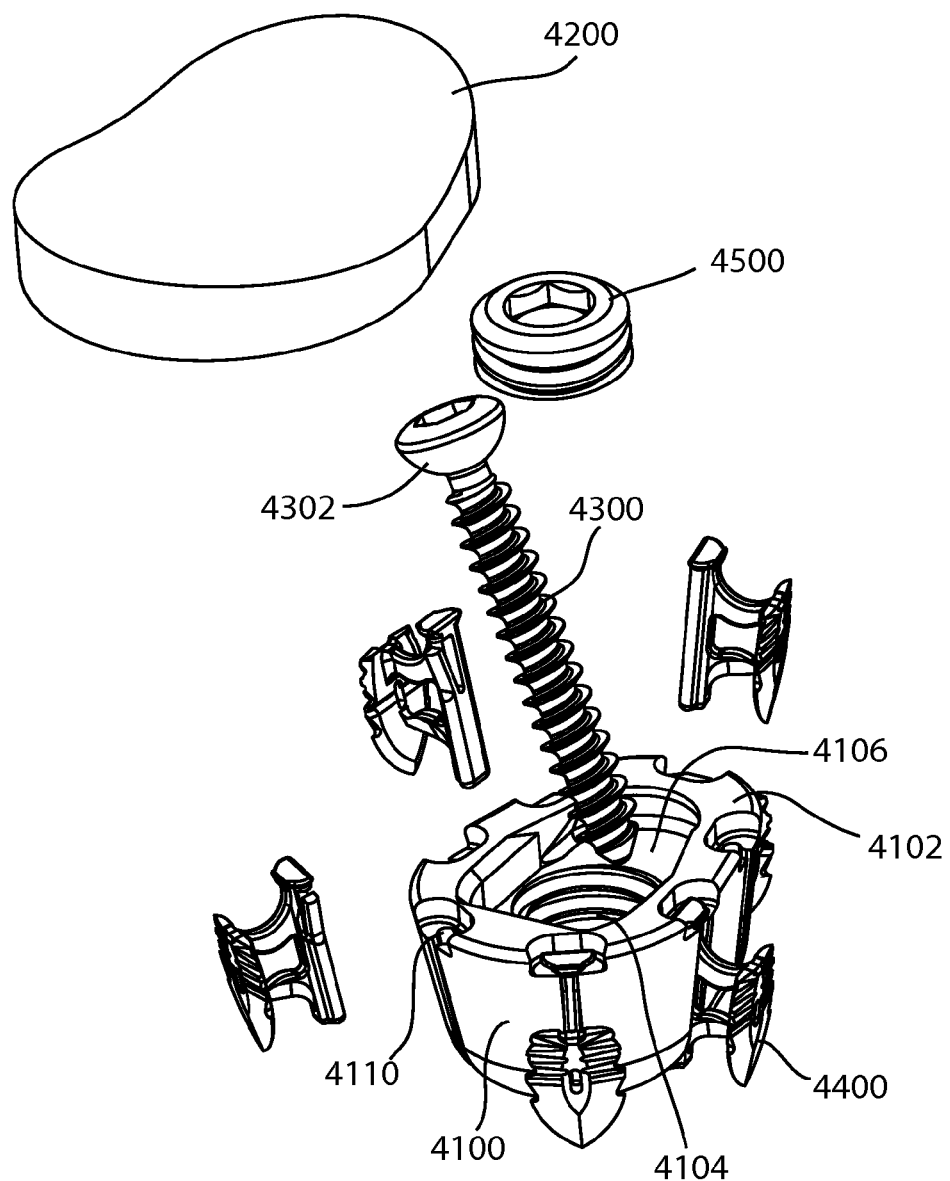
FIG. 55 is an exploded perspective view of the system of FIG. 54.
Figure 56:
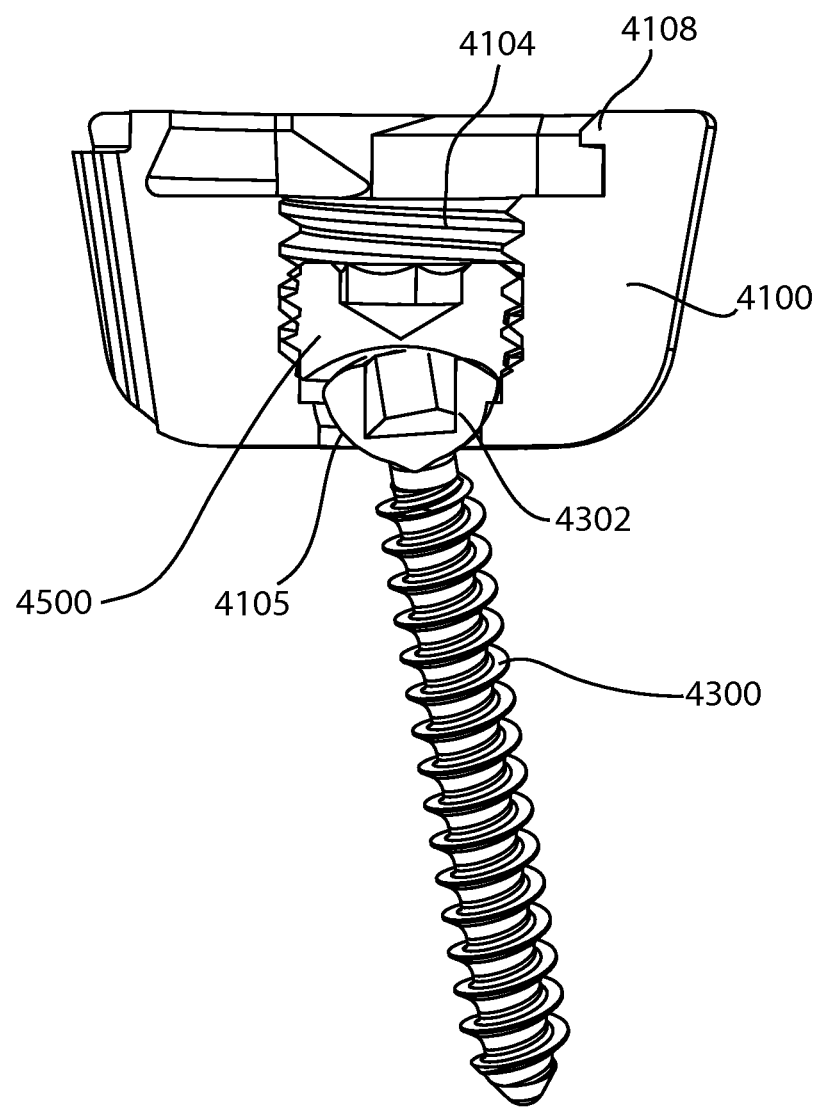
FIG. 56 is a cross sectional view of the vault and screw of FIG. 54.

Referring to FIGS. 54-56, an alternate embodiment of a glenoid vault system 4000 is depicted. The system 4000 includes a vault 4100 that may be pear-shaped, but may also be ovoid, spherical, cylindrical or many other shapes. The shape of the vault 4100 may depend on the bone preparation and the patient anatomy. The system also includes an articulating component 4200, a screw 4300, which may be a scapular spine screw, blade anchors 4400 as previously described herein, and a locking nut 4500.

The vault 4100 may comprise a circumferential wall 4102 defining the shape of the vault and encircling a central hole 4104 and an articulating void 4106 adjacent to and proximal the central hole 4104. The central hole 4104 may be cylindrical and may threadably or slidably receive the screw 4300. A screw seat 4105 (refer to FIG. 56) sits toward a distal end of the central hole 4104 and engages a head of the screw 4302 and allows the screw 4300 to pivot to secure the vault 4100 to the best bone. The locking nut 4500 is threaded and short and threadably engages the central hole 4104 locking the screw 4300 in place and preventing back-out. The locking nut 4500 fits at least partially, if not entirely, within the central hole 4104.

The articulating void 4106 provides a space for the articulating member 4200 to engage and lock to the vault 4100. The articulating void 4106 defined by the wall 4102 may have the same shape as the vault 4100. The void 4106 may taper, providing an overhang 4108 of the wall 4102 to provide a snap fit for engaging the articulating component 4200. The wall 4102 may also include an engagement ring similar to those embodiments previously described that protrudes toward the central hole 4104 into the void 4106.

Multiple tracks 4110 may be embedded in the outside of the wall 4102. The tracks may be substantially similar as the tracks 3416, 3102 previously described herein and interact with the blade anchors 4400 in substantially the same manner as previously described herein.

Figure 57:
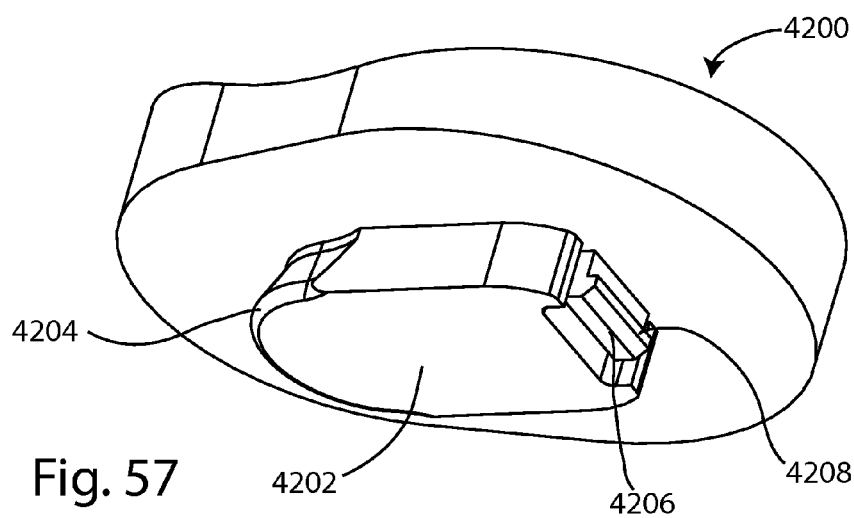
FIG. 57 is a bottom perspective view of the glenoid of the system of FIG. 54.

Referring to FIG. 57, the articulating component 4200 may be similar to those embodiments previously described with the exception of the post. A post 4202 extends from the bone facing side of the articulating component 4200 but may form a larger footprint from those posts previously disclosed. The post 4202 may include a first locking mechanism 4204 and a second locking mechanism 4206. The first locking mechanism 4204 is a reverse taper that extends out from where the post initially protrudes from the bone facing side of the articulating component 4200. On the opposite side of the post 4202 is the second locking mechanism 4206 that comprises a shoulder 4208 to snap into the void 4106 below the overhang 4108 of the wall 4102.

Figure 58:
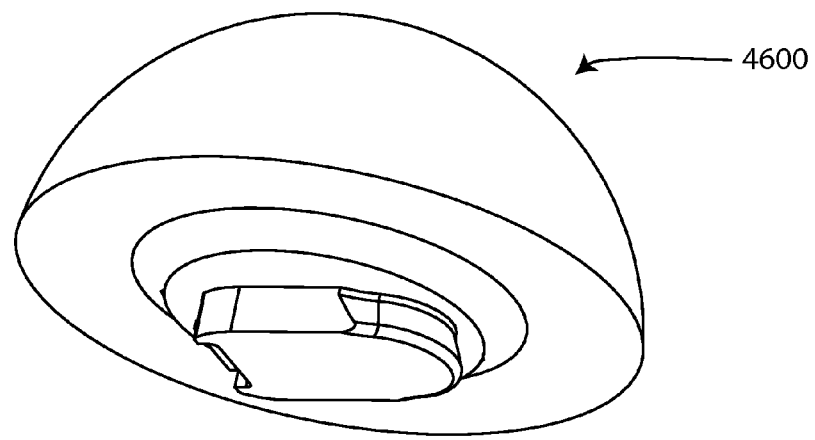
FIG. 58 is a bottom perspective view of a glenosphere that may be attached to the vault system of FIG. 54 in place of the glenoid.

Referring to FIG. 58, the articulating glenosphere 4600 shows a similar engagement feature as the articulating component 4200 and engages the vault 4100 in substantially the same manner as the articulating component 4200. The articulating component 4200 and glenosphere 4600 are reversibly locked to the vault so revision surgeries are easily accomplished without having to remove the vault 4100.

One method for implanting the vault system 4000 is to prepare the bone for the vault 4100 and securing the vault to the bone with the screw 4300. After securing the vault 4300 the locking nut 4500 locks the screw into place. The blade anchors 4400 may insert into the bone before, during or after the screw 4300 is inserted or fixed. The articulating component 4200 or glenosphere 4600 is then locked to the vault. The order in which the different components are secured is meant to be illustrative and not restrictive and the order may change within the scope of the system 4000.

In all embodiments described within this specification it will be appreciated that any articulating component or glenosphere will interact with the vaults in such a manner to allow for easy attachment while maintaining a robust design. The engagement allows for interchangeability from an articulating component to a glenosphere for easy revision. The engagement described previously with a snap fit or seal, or other locking means including a Morse taper (not shown) which may not require an engagement ring, of either the articulating component post or the glenosphere post engaging the appropriate AP/horizontal or SI/vertical component with the groove and or ring.

The features of all of the different systems may include the following: the vertical member width may be less than 6 mm; the horizontal member width may be less than or equal to 5 mm; overall vault depth may be less than 20 mm; the central portion or central ring diameter may be less than 9 mm; the central hole or central bore may be used for a scapular spine screw; and the cross members/components length or anchor sizing can be varied.

The present embodiments may be embodied in other specific forms without departing from its spirit or essential characteristics. It is appreciated that various features of the above described examples and embodiments may be mixed and matched to form a variety of other combinations and alternatives. It is also appreciated that this system should not be limited simply to shoulder replacement, revision or repair and may easily be adapted to other joint replacement technology, including, but not limited to hip repair. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A joint prosthesis configured to couple to one of an articulating component and a glenosphere, each of the articulating component and the glenosphere including a post, the post including at least one of a protrusive ring and a cutout ring, the joint prosthesis comprising:
    a vertical component, wherein the vertical component comprises a body comprising a bore extending at least partially through the body in a longitudinal direction and at least one vertical component arm extending from the body; and
    a horizontal component, wherein the horizontal component comprises a wall defining a hole, an engagement ring positioned on the wall, the engagement ring extending at least one of toward a center of the hole and away from the center of the hole, the engagement ring being configured to engage the at least one of the protrusive ring and the cutout ring on the post of the one of the articulating component and the glenosphere, and at least one horizontal component arm extending from the wall;
    wherein the vertical component and the horizontal component are configured to engage at the body of the vertical component and the wall of the hole of the horizontal component.

2. The joint prosthesis of claim 1, wherein the body is a central ring, the bore is a central bore and the hole is a central hole.

3. The joint prosthesis of claim 1, wherein the vertical component and horizontal component form a cruciate.

4. The joint prosthesis of claim 1, wherein the horizontal component is configured to be rotatable in relation to the vertical component about the central ring.

5. The joint prosthesis of claim 1, wherein the at least one vertical component arm further comprises a first lateral bore separate from the central bore.

6. The joint prosthesis of claim 5, wherein the at least one vertical component arm comprises a second vertical component arm wherein the second vertical component arm comprises a second lateral bore separate from the first lateral bore and separate from the central bore.

7. The joint prosthesis of claim 6, wherein the first and second lateral bores are configured to receive screws.

8. The joint prosthesis of claim 6, wherein the at least one horizontal component arm further comprises a third lateral bore separate from the central hole.

9. The joint prosthesis of claim 8, wherein the at least one horizontal component arm comprises a second horizontal component arm wherein the second horizontal component arm comprises a fourth lateral bore separate from the third lateral bore and separate from the central hole.

10. The joint prosthesis of claim 9, wherein the third and fourth lateral bores are configured to receive screws.

11. The joint prosthesis of claim 1, wherein the horizontal component further comprises at least one keel extending substantially parallel to the central hole, wherein the at least one keel provides rotational stops of the horizontal member against the vertical member.

12. The joint prosthesis of claim 1, wherein the wall of the central hole comprises notches configured to engage the post of the one of the articulating component and the glenosphere, wherein the notches are configured to allow rotational orientation of the one of the articulating component and the glenosphere and to prevent rotation of the one of the articulating component and the glenosphere.

13. The joint prosthesis of claim 3, wherein the central hole comprises a polygonal opening configured to receive a polygon component, wherein the polygonal opening and polygon component are configured, in combination, to allow rotational orientation of one of the articulating component and the glenosphere and to prevent rotation of one of the articulating component and the glenosphere.

14. The joint prosthesis of claim 13, wherein the polygon component is hexagonal.

15. A joint prosthesis configured to couple to an articulating component, the articulating component including an articulating surface, a bone-facing surface spaced apart and facing an opposite direction from the articulating surface, a post extending from the bone-facing surface, and at least one partial augment extending from the bone-facing surface, the joint prosthesis comprising:
   a superior-inferior component, wherein the superior-inferior component comprises a central ring comprising a central bore and at least one superior-inferior component arm extending from the central ring;
   an anterior-posterior component configured to be coupled to the superior-inferior component, wherein the anterior-posterior component comprises a wall defining a central hole and at least one augment extending from the wall, the at least one augment including an articulating-facing side and a bone-facing side, the articulating-facing side including pockets configure to receive the partial augment of the articulating component.

16. The joint prosthesis of claim 15 wherein the superior-inferior component and the anterior-posterior component are configured to engage at the central ring of the superior-inferior component and the wall of the central hole of the anterior-posterior component.

17. The joint prosthesis of claim 15, wherein the at least one superior-inferior component arm further comprises a first lateral bore separate from the central bore.

18. The joint prosthesis of claim 17, wherein the at least one superior-inferior component arm comprises a second superior-inferior component arm wherein the second superior-inferior component arm comprises a second lateral bore separate from the first lateral bore and separate from the central bore.

19. The joint prosthesis of claim 18, wherein the first and second lateral bores are configured to receive screws.

20. The joint prosthesis of claim 15, wherein the at least one augment comprises a first hole separate from the central hole.

21. The joint prosthesis of claim 15, wherein the wall of the central hole comprises notches configured to engage the post of the articulating component, wherein the notches are configured to allow rotational orientation of the articulating component and to prevent rotation of the articulating component.

22. The joint prosthesis of claim 15, wherein the wall of the central hole further comprises an engagement ring positioned on the wall, the engagement ring configured to engage the post of the articulating component.

23. A joint prosthesis configured to couple to one of an articulating component and a glenosphere, each of the articulating component and the glenosphere including a post, the post including notches, the joint prosthesis comprising:
   a superior-inferior component, wherein the superior-inferior component comprising a central ring comprising a central bore and at least one superior-inferior component arm extending from the central ring; and
   a cylindrical component comprising a wall defining a central hole, wherein the central hole includes notches at a proximal end of the central hole, the notches being configured to engage the notches on the post of one of the articulating component and the glenosphere;
   wherein at least a portion of the cylindrical component fits within the central ring of the superior-inferior component.

24. The joint prosthesis of claim 23, wherein the at least one superior-inferior component arm further comprises a first lateral bore separate from the central bore.

25. The joint prosthesis of claim 24, wherein the at least one superior-inferior component arm comprises a second superior-inferior component arm wherein the second superior-inferior component arm comprises a second lateral bore separate from the first lateral bore and separate from the central bore.

26. The joint prosthesis of claim 25, wherein the first and second lateral bores are configured to receive screws.

27. The joint prosthesis of claim 23, wherein the notches are configured to engage the post of one of the articulating component and the glenosphere, wherein the notches are configured to allow rotational orientation of one of the articulating component and the glenosphere and to prevent rotation of one of the articulating component and the glenosphere.

28. The joint prosthesis of claim 23, wherein the cylindrical component further comprises an engagement ring positioned on the wall, the engagement ring configured to engage the post of one of the articulating component and the glenosphere.

29. A joint prosthesis configured to couple to one of an articulating component and a glenosphere, each of the articulating component and the glenosphere including a post, the post including at least one of a protrusive ring and a cutout ring, the joint prosthesis comprising:
   a horizontal component, wherein the horizontal component comprises a central ring comprising a central bore and at least one horizontal component arm extending from the central ring; and
   a vertical component, wherein the vertical component comprises a cylindrical portion defining a central hole and at least one vertical component arm extending from the cylindrical portion, wherein the wall of the central hole further comprises an engagement ring extending at least one of toward a center of the hole and away from the center of the hole, the engagement ring being configured to engage the at least one of the protrusive ring and the cutout ring on the post of one of the articulating component and the glenosphere;
   wherein the horizontal component and the vertical component are configured to engage at the central ring of the horizontal component and the cylindrical portion of the vertical component.

30. The joint prosthesis of claim 29, wherein the vertical component is configured to be rotatable in relation to the horizontal component about the central ring.

31. The joint prosthesis of claim 29, wherein the at least one horizontal component arm further comprises a first lateral passage separate from the central bore.

32. The joint prosthesis of claim 31, wherein the at least one horizontal component arm comprises a second horizontal component arm wherein the second horizontal component arm comprises a second lateral passage separate from the first lateral passage and separate from the central bore.

33. The joint prosthesis of claim 32, wherein the first and second lateral passage are configured to receive anchors.

34. The joint prosthesis of claim 33, wherein the anchors are screws.

35. The joint prosthesis of claim 32, wherein the at least one vertical component arm further comprises a third lateral passage separate from the central hole.

36. The joint prosthesis of claim 35, wherein the at least one vertical component arm comprises a second vertical component arm wherein the second vertical component arm comprises a fourth lateral passage separate from the third lateral passage and separate from the central hole.

37. The joint prosthesis of claim 36, wherein the third and fourth lateral bores are configured to receive anchors.

38. The joint prosthesis of claim 37, wherein the anchors are screws.

39. The joint prosthesis of claim 29, wherein the vertical component further comprises at least one of a roughened surface and an interrupted surface geometry for increased pull out resistance.

40. The joint prosthesis of claim 39, wherein the wall of the central hole comprises notches configured to engage the post of one of the articulating component and the glenosphere, wherein the notches are configured to allow rotational orientation of one of the articulating component and the glenosphere and to prevent rotation of one of the articulating component and the glenosphere.

41. A joint prosthesis configured to couple to one of an articulating component and a glenosphere, each of the articulating component and the glenosphere including a post, the post including at least one of a protrusive ring and a cutout ring, the joint prosthesis comprising:
    a superior-inferior component, wherein the superior-inferior component comprises a central ring comprising a central bore;
    a cylindrical component comprising a wall defining a central hole, wherein the wall of the central hole further comprises an engagement ring positioned on the wall, the engagement ring extending at least one of toward a center of the hole and away from the center of the hole, the engagement ring being configured to engage the at least one of the protrusive ring and the cutout ring on the post of the one of the articulating component and the glenosphere;
    wherein at least a portion of the cylindrical component fits within the central ring of the superior-inferior component.

42. The joint prosthesis of claim 41, wherein superior-inferior component further comprises at least one superior-inferior component arm extending from the central ring.

43. The joint prosthesis of claim 41, wherein the central hole comprises notches configured to engage one of the articulating component and the glenosphere.

44. The joint prosthesis of claim 1, wherein the at least one horizontal component arm further comprises a first lateral bore separate from the central hole.

45. The joint prosthesis of claim 29, wherein the at least one vertical component arm further comprises a first lateral passage separate from the central hole.

* * * * *